United States Patent
McMillen et al.

(10) Patent No.: US 10,362,989 B2
(45) Date of Patent: *Jul. 30, 2019

(54) SENSOR SYSTEM INTEGRATED WITH A GLOVE

(71) Applicant: BeBop Sensors, Inc., Berkeley, CA (US)

(72) Inventors: Keith A. McMillen, Berkeley, CA (US); Kyle Lobedan, Oakland, CA (US); Gregory Wille, Berkeley, CA (US); Florian Muller, Oakland, CA (US); Maxime Stinnett, Oakland, CA (US)

(73) Assignee: BeBop Sensors, Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/621,935

(22) Filed: Jun. 13, 2017

(65) Prior Publication Data

US 2017/0303853 A1    Oct. 26, 2017

Related U.S. Application Data

(63) Continuation-in-part of application No. 14/928,058, filed on Oct. 30, 2015, now Pat. No. 9,710,060, which
(Continued)

(51) Int. Cl.
*A61B 5/00* (2006.01)
*G01L 1/18* (2006.01)
(Continued)

(52) U.S. Cl.
CPC .......... *A61B 5/6806* (2013.01); *A61B 5/6843* (2013.01); *G01L 1/18* (2013.01);
(Continued)

(58) Field of Classification Search
CPC ...... A61B 2562/0247; A61B 2562/164; A61B 2562/046; A61B 2562/0261;
(Continued)

(56) References Cited

U.S. PATENT DOCUMENTS

| 4,294,014 A | 10/1981 | Baumann et al. |
| 4,438,291 A | 3/1984 | Eichelberger et al. |

(Continued)

FOREIGN PATENT DOCUMENTS

| CN | 200980381 Y | 11/2007 |
| CN | 201920728 U | 8/2011 |

(Continued)

OTHER PUBLICATIONS

U.S. Office Action dated Sep. 12, 2012 issued in U.S. Appl. No. 12/904,657.
(Continued)

*Primary Examiner* — Dismery Mercedes
(74) *Attorney, Agent, or Firm* — Weaver Austin Villeneuve & Sampson LLP

(57) ABSTRACT

Sensor systems are described that are designed to be integrated with gloves for the human hand. An array of sensors detects forces associated with action of a hand in the glove, and associated circuitry generates corresponding control information that may be used to control a wide variety of processes and devices.

34 Claims, 18 Drawing Sheets

Related U.S. Application Data is a continuation-in-part of application No. 14/671,821, filed on Mar. 27, 2015, now Pat. No. 9,753,568, which is a continuation-in-part of application No. 14/299,976, filed on Jun. 9, 2014, now Pat. No. 9,965,076.

(60) Provisional application No. 62/072,798, filed on Oct. 30, 2014.

(51) Int. Cl.

| | | |
|---|---|---|
| *G06F 3/01* | (2006.01) | |
| *H03K 17/96* | (2006.01) | |
| *G06F 3/045* | (2006.01) | |
| *G01L 5/22* | (2006.01) | |
| *G01L 25/00* | (2006.01) | |
| *G01L 1/22* | (2006.01) | |
| *A61B 34/00* | (2016.01) | |
| *A61B 5/11* | (2006.01) | |
| *A61B 90/00* | (2016.01) | |

(52) U.S. Cl.
CPC .......... *G01L 1/2206* (2013.01); *G01L 1/2293* (2013.01); *G01L 5/228* (2013.01); *G01L 25/00* (2013.01); *G06F 3/014* (2013.01); *G06F 3/045* (2013.01); *H03K 17/964* (2013.01); *A61B 5/1114* (2013.01); *A61B 34/76* (2016.02); *A61B 2034/741* (2016.02); *A61B 2090/064* (2016.02); *A61B 2562/0247* (2013.01); *A61B 2562/0261* (2013.01); *Y10T 29/49156* (2015.01)

(58) Field of Classification Search
CPC ... A61B 5/6806; A61B 5/6804; A61B 5/1114; A61B 5/7475; A61B 5/4528; A61B 5/6825; A61B 5/6826; A61B 2034/741; A61B 2090/064; A61B 2090/065; G01L 1/146; G01L 1/205; G01L 1/2287; G01L 1/2206; G01L 1/22; G01L 1/18; G01L 1/144; G01L 5/228; G06F 3/014; G06F 3/016; G06F 2203/0331
See application file for complete search history.

(56) References Cited

U.S. PATENT DOCUMENTS

| | | |
|---|---|---|
| 4,489,302 A | 12/1984 | Eventoff |
| 4,693,530 A | 9/1987 | Stillie et al. |
| 4,745,301 A | 5/1988 | Michalchik |
| 4,790,968 A | 12/1988 | Ohkawa et al. |
| 4,852,443 A | 8/1989 | Duncan et al. |
| 5,033,291 A | 7/1991 | Podoloff et al. |
| 5,128,880 A | 7/1992 | White |
| 5,131,306 A | 7/1992 | Yamamoto |
| 5,159,159 A | 10/1992 | Asher |
| 5,219,292 A | 6/1993 | Dickirson et al. |
| 5,237,520 A | 8/1993 | White |
| 5,288,938 A | 2/1994 | Wheaton |
| 5,316,017 A | 5/1994 | Edwards et al. |
| 5,386,720 A | 2/1995 | Toda et al. |
| 5,429,092 A | 7/1995 | Kamei |
| 5,571,973 A | 11/1996 | Taylot |
| 5,578,766 A | 11/1996 | Kondo |
| 5,624,132 A | 4/1997 | Blackburn et al. |
| 5,659,395 A | 8/1997 | Brown et al. |
| 5,695,859 A | 12/1997 | Burgess |
| 5,729,905 A | 3/1998 | Mathiasmeier et al. |
| 5,822,223 A | 10/1998 | Genest |
| 5,866,829 A | 2/1999 | Pecoraro |
| 5,878,359 A | 3/1999 | Takeda |
| 5,943,044 A | 8/1999 | Martinelli et al. |
| 5,989,700 A | 11/1999 | Krivopal |
| 6,029,358 A | 2/2000 | Mathiasmeier et al. |
| 6,032,109 A | 2/2000 | Ritmiller, III |
| 6,049,327 A * | 4/2000 | Walker .................. G06F 3/014 |
| | | 345/158 |
| 6,087,930 A | 7/2000 | Kulka et al. |
| 6,121,869 A | 9/2000 | Burgess |
| 6,141,643 A | 10/2000 | Harmon |
| 6,155,120 A | 12/2000 | Taylor |
| 6,215,055 B1 | 4/2001 | Saravis |
| 6,216,545 B1 | 4/2001 | Taylor |
| 6,304,840 B1 | 10/2001 | Vance et al. |
| 6,331,893 B1 | 12/2001 | Brown et al. |
| 6,360,615 B1 * | 3/2002 | Smela .................. A61B 5/1124 |
| | | 73/862.474 |
| 6,452,479 B1 | 9/2002 | Sandbach |
| 6,486,776 B1 | 11/2002 | Pollack et al. |
| 6,687,523 B1 | 2/2004 | Jayaramen et al. |
| 6,763,320 B2 | 7/2004 | Kimble |
| 6,815,602 B2 | 11/2004 | De Franco |
| 6,822,635 B2 | 11/2004 | Shahoian et al. |
| 6,829,942 B2 | 12/2004 | Yanai et al. |
| 6,964,205 B2 | 11/2005 | Papakostas et al. |
| 7,037,268 B1 | 5/2006 | Sleva et al. |
| 7,066,887 B2 | 6/2006 | Flesch et al. |
| 7,109,068 B2 | 9/2006 | Akram et al. |
| 7,113,856 B2 | 9/2006 | Theiss et al. |
| 7,138,976 B1 | 11/2006 | Bouzit et al. |
| 7,157,640 B2 | 1/2007 | Baggs |
| 7,302,866 B1 | 12/2007 | Malkin et al. |
| 7,311,009 B2 | 12/2007 | Kotovsky |
| 7,332,670 B2 | 2/2008 | Fujiwara et al. |
| 7,409,256 B2 | 8/2008 | Lin et al. |
| 7,439,465 B2 | 10/2008 | Parkinson |
| 7,493,230 B2 | 2/2009 | Schwartz et al. |
| 7,536,794 B2 | 5/2009 | Hay et al. |
| 7,584,666 B2 | 9/2009 | Kim et al. |
| 7,608,776 B2 | 10/2009 | Ludwig |
| 7,719,007 B2 | 5/2010 | Tompkins et al. |
| 7,726,199 B2 | 6/2010 | Shkel et al. |
| 7,754,956 B2 | 7/2010 | Gain et al. |
| 7,780,541 B2 | 8/2010 | Bauer |
| 7,855,718 B2 | 12/2010 | Westerman |
| 7,928,312 B2 | 4/2011 | Sharma |
| 7,984,544 B2 | 7/2011 | Rosenberg |
| 8,109,149 B2 | 2/2012 | Kotovsky |
| 8,117,922 B2 | 2/2012 | Xia et al. |
| 8,120,232 B2 | 2/2012 | Daniel et al. |
| 8,127,623 B2 | 3/2012 | Son et al. |
| 8,161,826 B1 | 4/2012 | Taylor |
| 8,162,857 B2 * | 4/2012 | Lanfermann ...... A41D 13/1281 |
| | | 600/595 |
| 8,250,934 B2 | 8/2012 | Sakurai |
| 8,274,485 B2 | 9/2012 | Liu et al. |
| 8,346,684 B2 | 1/2013 | Mirbach et al. |
| 8,368,505 B2 | 2/2013 | Deppiesse et al. |
| 8,448,530 B2 | 5/2013 | Leuenberger et al. |
| 8,479,585 B2 | 7/2013 | Shaw-Klein |
| 8,536,880 B2 | 9/2013 | Philipp |
| 8,571,827 B2 | 10/2013 | Jang et al. |
| 8,661,917 B2 | 3/2014 | Jheng et al. |
| 8,680,390 B2 | 3/2014 | McMillen et al. |
| 8,813,579 B2 | 8/2014 | Aufrere |
| 8,857,274 B2 | 10/2014 | Mamigonians |
| 8,880,358 B2 * | 11/2014 | Cunningham ........ A61B 5/1116 |
| | | 702/41 |
| 8,884,913 B2 | 11/2014 | Saynac et al. |
| 8,892,051 B2 | 11/2014 | Yi et al. |
| 8,893,565 B2 | 11/2014 | White et al. |
| 8,904,876 B2 | 12/2014 | Taylor et al. |
| 8,925,392 B2 | 1/2015 | Esposito et al. |
| 8,925,393 B2 | 1/2015 | Cannard et al. |
| 8,928,014 B2 | 1/2015 | Tischler et al. |
| 8,945,328 B2 | 2/2015 | Longinotti-Buitoni et al. |
| 8,947,889 B2 | 2/2015 | Kelley et al. |
| 8,950,265 B2 | 2/2015 | Dunn et al. |
| 8,964,205 B2 | 2/2015 | Shimizu |
| 8,970,513 B2 | 3/2015 | Kwon et al. |
| 9,032,804 B2 | 5/2015 | Granado et al. |

(56) References Cited

U.S. PATENT DOCUMENTS

| | | |
|---|---|---|
| 9,038,482 B2 | 5/2015 | Xia et al. |
| 9,075,404 B2 | 7/2015 | McMillen et al. |
| 9,076,419 B2 | 7/2015 | McMillen et al. |
| 9,112,058 B2 | 8/2015 | Bao et al. |
| 9,116,569 B2 | 8/2015 | William et al. |
| 9,164,586 B2 | 10/2015 | Zellers et al. |
| 9,182,302 B2 | 11/2015 | Lim et al. |
| 9,271,665 B2 | 3/2016 | Sarrafzadeh et al. |
| 9,413,376 B2* | 8/2016 | Lowe ............... G06F 3/04886 |
| 9,417,693 B2* | 8/2016 | Seth .................. G06F 3/017 |
| 9,442,614 B2 | 9/2016 | McMillen |
| 9,480,582 B2* | 11/2016 | Lundborg ............ A61F 2/583 |
| 9,529,433 B2 | 12/2016 | Shankar et al. |
| 9,546,921 B2 | 1/2017 | McMillen et al. |
| 9,582,035 B2* | 2/2017 | Connor ................ G06F 1/163 |
| 9,612,102 B2* | 4/2017 | Reese ................. G01B 7/22 |
| 9,652,101 B2 | 5/2017 | McMillen et al. |
| 9,682,856 B2 | 6/2017 | Whitesides et al. |
| 9,696,833 B2 | 7/2017 | McMillen |
| 9,710,060 B2* | 7/2017 | McMillen .......... H03K 17/964 |
| 9,721,553 B2 | 8/2017 | McMillen et al. |
| 9,753,568 B2 | 9/2017 | McMillen |
| 9,756,895 B2 | 9/2017 | Rice et al. |
| 9,827,996 B2 | 11/2017 | McMillen |
| 9,836,151 B2 | 12/2017 | McMillen |
| 9,863,823 B2 | 1/2018 | McMillen |
| 9,891,718 B2* | 2/2018 | Connor ................ G06F 3/017 |
| 9,965,076 B2 | 5/2018 | McMillen |
| 9,970,832 B2* | 5/2018 | Hong .................. G01B 7/16 |
| 9,993,921 B2* | 6/2018 | Lessing .............. B25J 9/142 |
| 10,076,143 B2* | 9/2018 | Marriott ........... A63B 21/0421 |
| 10,082,381 B2 | 9/2018 | McMillen et al. |
| 10,114,493 B2 | 10/2018 | McMillen et al. |
| 10,268,315 B2 | 4/2019 | McMillen et al. |
| 10,282,011 B2 | 5/2019 | McMillen et al. |
| 2002/0078757 A1 | 6/2002 | Hines et al. |
| 2002/0180578 A1 | 12/2002 | Sandbach |
| 2004/0031180 A1 | 2/2004 | Ivanov |
| 2004/0093746 A1 | 5/2004 | Varsallona |
| 2004/0183648 A1 | 9/2004 | Weber et al. |
| 2004/0189145 A1 | 9/2004 | Pletner et al. |
| 2004/0252007 A1 | 12/2004 | Lussey et al. |
| 2005/0109095 A1 | 5/2005 | Sinnett |
| 2005/0220673 A1 | 10/2005 | Thaysen |
| 2007/0063992 A1* | 3/2007 | Lundquist .............. G06F 1/163 345/174 |
| 2007/0129776 A1 | 6/2007 | Robins et al. |
| 2007/0151348 A1 | 7/2007 | Zdeblick et al. |
| 2007/0188179 A1 | 8/2007 | Deangelis et al. |
| 2007/0188180 A1 | 8/2007 | Deangelis et al. |
| 2007/0202765 A1 | 8/2007 | Krans et al. |
| 2007/0234888 A1 | 10/2007 | Rotolo de Moraes |
| 2008/0069412 A1 | 3/2008 | Champagne et al. |
| 2008/0158145 A1 | 7/2008 | Westerman |
| 2008/0189827 A1 | 8/2008 | Bauer |
| 2008/0254824 A1 | 10/2008 | Moraes |
| 2009/0013793 A1 | 1/2009 | Kim et al. |
| 2009/0049980 A1 | 2/2009 | Sharma |
| 2009/0134966 A1 | 5/2009 | Baker |
| 2009/0237374 A1 | 9/2009 | Li et al. |
| 2009/0272197 A1 | 11/2009 | Ridao Granado et al. |
| 2009/0301190 A1 | 12/2009 | Ross, Jr. et al. |
| 2009/0303400 A1 | 12/2009 | Hou et al. |
| 2010/0066572 A1 | 3/2010 | Dietz et al. |
| 2010/0123686 A1 | 5/2010 | Klinghult et al. |
| 2010/0134327 A1 | 6/2010 | Dinh et al. |
| 2010/0149108 A1 | 6/2010 | Hotelling et al. |
| 2010/0179724 A1 | 7/2010 | Weston |
| 2010/0199777 A1 | 8/2010 | Hooper et al. |
| 2010/0242274 A1 | 9/2010 | Rosenfeld et al. |
| 2010/0274447 A1 | 10/2010 | Stumpf |
| 2010/0286951 A1 | 11/2010 | Danenberg et al. |
| 2010/0292945 A1 | 11/2010 | Reynolds et al. |
| 2010/0315337 A1 | 12/2010 | Ferren et al. |
| 2011/0005090 A1* | 1/2011 | Lee ................. G01D 5/145 33/1 PT |
| 2011/0088535 A1 | 4/2011 | Zarimis |
| 2011/0088536 A1 | 4/2011 | McMillen et al. |
| 2011/0107771 A1 | 5/2011 | Crist et al. |
| 2011/0141052 A1 | 6/2011 | Bernstein et al. |
| 2011/0153261 A1 | 6/2011 | Jang et al. |
| 2011/0199284 A1 | 8/2011 | Davis et al. |
| 2011/0221564 A1 | 9/2011 | Deppiesse et al. |
| 2011/0241850 A1 | 10/2011 | Bosch et al. |
| 2011/0246028 A1 | 10/2011 | Lisseman et al. |
| 2011/0260994 A1 | 10/2011 | Saynac et al. |
| 2011/0271772 A1 | 11/2011 | Parks et al. |
| 2011/0279409 A1 | 11/2011 | Salaverry et al. |
| 2011/0292049 A1* | 12/2011 | Muravsky ............ G06F 3/014 345/440 |
| 2011/0302694 A1* | 12/2011 | Wang ................ A61B 5/103 2/160 |
| 2012/0007831 A1 | 1/2012 | Chang et al. |
| 2012/0024132 A1 | 2/2012 | Wallace et al. |
| 2012/0026124 A1 | 2/2012 | Li et al. |
| 2012/0055257 A1 | 3/2012 | Shaw-Klein |
| 2012/0090408 A1 | 4/2012 | Jheng et al. |
| 2012/0143092 A1 | 6/2012 | Xia et al. |
| 2012/0191554 A1 | 7/2012 | Xia et al. |
| 2012/0197161 A1 | 8/2012 | Xia et al. |
| 2012/0198949 A1 | 8/2012 | Xia et al. |
| 2012/0222498 A1 | 9/2012 | Mamigonians |
| 2012/0234105 A1 | 9/2012 | Taylor |
| 2012/0283979 A1 | 11/2012 | Bruekers et al. |
| 2012/0296528 A1 | 11/2012 | Wellhoefer et al. |
| 2012/0297885 A1 | 11/2012 | Hou et al. |
| 2012/0299127 A1 | 11/2012 | Fujii et al. |
| 2012/0312102 A1 | 12/2012 | Alvarez et al. |
| 2012/0323501 A1 | 12/2012 | Sarrafzadeh et al. |
| 2013/0009905 A1 | 1/2013 | Castillo et al. |
| 2013/0055482 A1 | 3/2013 | D'Aprile et al. |
| 2013/0082970 A1 | 4/2013 | Frey et al. |
| 2013/0085394 A1 | 4/2013 | Corbett, III et al. |
| 2013/0113057 A1 | 5/2013 | Taylor |
| 2013/0113704 A1 | 5/2013 | Sarrafzadeh et al. |
| 2013/0165809 A1 | 6/2013 | Abir |
| 2013/0192071 A1 | 8/2013 | Esposito et al. |
| 2013/0203201 A1 | 8/2013 | Britton et al. |
| 2013/0211208 A1 | 8/2013 | Varadan et al. |
| 2013/0214365 A1 | 8/2013 | Schlarmann et al. |
| 2013/0239787 A1 | 9/2013 | McMillen et al. |
| 2013/0274985 A1 | 10/2013 | Lee et al. |
| 2013/0275057 A1 | 10/2013 | Perlin et al. |
| 2013/0327560 A1 | 12/2013 | Ichiki |
| 2013/0340598 A1 | 12/2013 | Marquez et al. |
| 2014/0007704 A1 | 1/2014 | Granado et al. |
| 2014/0007706 A1 | 1/2014 | Aufrere et al. |
| 2014/0013865 A1 | 1/2014 | White et al. |
| 2014/0026678 A1 | 1/2014 | Cannard et al. |
| 2014/0033829 A1 | 2/2014 | Xia et al. |
| 2014/0090488 A1* | 4/2014 | Taylor ................ G01L 1/18 73/862.625 |
| 2014/0104776 A1 | 4/2014 | Clayton et al. |
| 2014/0104792 A1 | 4/2014 | Jeziorek |
| 2014/0107966 A1 | 4/2014 | Xia et al. |
| 2014/0107967 A1 | 4/2014 | Xia et al. |
| 2014/0107968 A1 | 4/2014 | Xia et al. |
| 2014/0125124 A1 | 5/2014 | Verner |
| 2014/0130593 A1 | 5/2014 | Ciou et al. |
| 2014/0150573 A1 | 6/2014 | Cannard et al. |
| 2014/0182170 A1 | 7/2014 | Wawrousek et al. |
| 2014/0195023 A1 | 7/2014 | Statham et al. |
| 2014/0215684 A1 | 8/2014 | Hardy et al. |
| 2014/0222173 A1 | 8/2014 | Giedwoyn et al. |
| 2014/0222243 A1 | 8/2014 | McMillen et al. |
| 2014/0238153 A1* | 8/2014 | Wood .................. G06F 3/011 73/862.627 |
| 2014/0240214 A1* | 8/2014 | Liu .................. G06F 3/014 345/156 |
| 2014/0264407 A1 | 9/2014 | Tischler et al. |

(56) References Cited

U.S. PATENT DOCUMENTS

| | | | |
|---|---|---|---|
| 2014/0318699 A1* | 10/2014 | Longinotti-Buitoni | A61B 5/0002 156/247 |
| 2014/0347076 A1 | 11/2014 | Barton et al. | |
| 2015/0035743 A1 | 2/2015 | Rosener | |
| 2015/0084873 A1 | 3/2015 | Hagenbuch et al. | |
| 2015/0086955 A1 | 3/2015 | Poniatowski et al. | |
| 2015/0130698 A1* | 5/2015 | Burgess | G06F 1/163 345/156 |
| 2015/0168238 A1 | 6/2015 | Raut et al. | |
| 2015/0177080 A1 | 6/2015 | Esposito et al. | |
| 2015/0248159 A1* | 9/2015 | Luo | G06F 3/014 345/156 |
| 2015/0261372 A1 | 9/2015 | McMillen et al. | |
| 2015/0316434 A1 | 11/2015 | McMillen et al. | |
| 2015/0317964 A1 | 11/2015 | McMillen et al. | |
| 2015/0328492 A1* | 11/2015 | Marriott | A63B 21/0421 482/124 |
| 2015/0330855 A1 | 11/2015 | Daniecki et al. | |
| 2015/0331512 A1 | 11/2015 | McMillen et al. | |
| 2015/0331522 A1 | 11/2015 | McMillen et al. | |
| 2015/0331523 A1 | 11/2015 | McMillen et al. | |
| 2015/0331524 A1 | 11/2015 | McMillen et al. | |
| 2015/0331533 A1 | 11/2015 | McMillen et al. | |
| 2015/0370396 A1 | 12/2015 | Hotelling et al. | |
| 2016/0052131 A1* | 2/2016 | Lessing | B25J 9/142 361/679.01 |
| 2016/0054798 A1* | 2/2016 | Messingher | G06F 3/012 345/156 |
| 2016/0070347 A1 | 3/2016 | McMillen et al. | |
| 2016/0073539 A1 | 3/2016 | Driscoll et al. | |
| 2016/0147352 A1 | 5/2016 | Filiz et al. | |
| 2016/0162022 A1* | 6/2016 | Seth | G06F 3/017 345/156 |
| 2016/0169754 A1* | 6/2016 | Kowalewski | G01L 5/228 73/862.046 |
| 2016/0175186 A1 | 6/2016 | Shadduck | |
| 2016/0187973 A1* | 6/2016 | Shankar | G06F 3/014 345/156 |
| 2016/0209441 A1 | 7/2016 | Mazzeo et al. | |
| 2016/0238547 A1 | 8/2016 | Park et al. | |
| 2016/0246369 A1* | 8/2016 | Osman | A63F 13/212 |
| 2016/0252412 A1 | 9/2016 | McMillen et al. | |
| 2016/0270727 A1 | 9/2016 | Berg et al. | |
| 2016/0278709 A1 | 9/2016 | Ridao Granado et al. | |
| 2016/0313798 A1* | 10/2016 | Connor | G06F 3/017 |
| 2016/0318356 A1 | 11/2016 | McMillen et al. | |
| 2016/0340534 A1 | 11/2016 | Wijesundara et al. | |
| 2016/0375910 A1 | 12/2016 | McMillen et al. | |
| 2017/0000369 A1* | 1/2017 | Hyde | A61B 5/04085 |
| 2017/0038881 A1 | 2/2017 | McMillen | |
| 2017/0056644 A1* | 3/2017 | Chahine | A61N 1/0452 |
| 2017/0086519 A1* | 3/2017 | Vigano' | D02G 3/00 |
| 2017/0108929 A1 | 4/2017 | Sinko et al. | |
| 2017/0110103 A1 | 4/2017 | McMillen et al. | |
| 2017/0127736 A1* | 5/2017 | Roberts | A41D 1/002 |
| 2017/0167931 A1 | 6/2017 | McMillen et al. | |
| 2017/0176267 A1* | 6/2017 | Keller | G01L 1/144 |
| 2017/0212638 A1 | 7/2017 | McMillen | |
| 2017/0215495 A1* | 8/2017 | Okumiya | A41D 19/0013 |
| 2017/0305301 A1 | 10/2017 | McMillen et al. | |
| 2018/0015932 A1 | 1/2018 | McMillen et al. | |
| 2018/0094991 A1 | 4/2018 | McMillen et al. | |
| 2018/0263563 A1 | 9/2018 | McMillen et al. | |
| 2019/0034019 A1 | 1/2019 | McMillen et al. | |

FOREIGN PATENT DOCUMENTS

| | | |
|---|---|---|
| CN | 102551728 A | 7/2012 |
| CN | 202396601 U | 8/2012 |
| CN | 203234132 U | 10/2013 |
| CN | 102406280 B | 3/2014 |
| DE | 102 12 023 A1 | 10/2003 |
| DE | 11 2010 004 038 T5 | 9/2012 |
| EP | 0 014 022 B1 | 11/1984 |
| EP | 0 211 984 | 3/1987 |
| EP | 2 682 724 A1 | 1/2014 |
| JP | S47-18925 | 5/1972 |
| JP | H04-011666 A | 1/1992 |
| JP | H06-323929 A | 11/1994 |
| JP | H08-194481 A | 7/1996 |
| JP | H10-198503 A | 7/1998 |
| JP | 2000-267664 A | 9/2000 |
| JP | 2007-503052 A | 2/2007 |
| JP | 2008-515008 A | 5/2008 |
| JP | 2009-543030 A | 12/2009 |
| JP | 2011-502313 A | 1/2011 |
| JP | 2012-521550 A | 9/2012 |
| JP | 2012-220315 A | 11/2012 |
| JP | 2014-077662 A | 5/2014 |
| KR | 10-2007-0008500 A | 1/2007 |
| KR | 100865148 B1 | 10/2008 |
| KR | 10-1362742 B1 | 2/2014 |
| KR | 10-2014-0071693 A | 6/2014 |
| NL | 8900820 A | 11/1990 |
| RU | 2 533 539 C1 | 11/2014 |
| WO | WO 99/020179 A1 | 4/1999 |
| WO | WO 2007/024875 A2 | 3/2007 |
| WO | WO 2008/032661 | 3/2008 |
| WO | WO 2009/155891 A1 | 12/2009 |
| WO | WO 2011/047171 A2 | 4/2011 |
| WO | WO 2013/181474 | 12/2013 |
| WO | WO 2015/175317 A1 | 11/2015 |
| WO | WO 2016/070078 A1 | 5/2016 |
| WO | WO 2016/138234 A1 | 9/2016 |
| WO | WO 2016/176307 A1 | 11/2016 |
| WO | WO 2016/210173 A1 | 12/2016 |
| WO | WO 2017/066096 A1 | 4/2017 |
| WO | WO 2017/184367 A1 | 10/2017 |

OTHER PUBLICATIONS

U.S. Office Action dated Apr. 15, 2013 issued in U.S. Appl. No. 12/904,657.

U.S. Notice of Allowance dated Nov. 8, 2013 issued in U.S. Appl. No. 12/904,657.

U.S. Office Action dated Mar. 12, 2015 issued in U.S. Appl. No. 14/173,617.

U.S. Notice of Allowance dated May 1, 2015 issued in U.S. Appl. No. 14/173,617.

U.S. Office Action dated Mar. 10, 2016 issued in U.S. Appl. No. 14/727,619.

U.S. Final Office Action dated Jul. 18, 2016 issued in U.S. Appl. No. 14/727,619.

U.S. Notice of Allowance dated Sep. 15, 2016 issued in U.S. Appl. No. 14/727,619.

Office Action dated Apr. 2, 2015 issued in U.S. Appl. No. 13/799,304.

U.S. Notice of Allowance dated Apr. 24, 2015 issued in U.S. Appl. No. 13/799,304.

U.S. Office Action dated Sep. 1, 2015 issued in U.S. Appl. No. 14/728,872.

U.S. Final Office Action dated Mar. 9, 2016 issued in U.S. Appl. No. 14/728,872.

U.S. Office Action dated Jun. 22, 2016 issued in U.S. Appl. No. 14/728,872.

U.S. Final Office Action dated Oct. 18, 2016 issued in U.S. Appl. No. 14/728,872.

U.S. Advisory Action dated Feb. 10, 2017 issued in U.S. Appl. No. 14/728,872.

U.S. Office Action dated May 19, 2017 issued in U.S. Appl. No. 14/728,872.

U.S. Office Action dated Jul. 25, 2016 issued in U.S. Appl. No. 14/728,873.

U.S. Office Action dated Dec. 30, 2016 issued in U.S. Appl. No. 14/728,873.

U.S. Final Office Action dated Mar. 31, 2017 issued in U.S. Appl. No. 14/728,873.

U.S. Advisory Action issued in U.S. Appl. No. 14/728,873 and Examiner initiated interview summary dated May 26, 2017.

(56) References Cited

OTHER PUBLICATIONS

U.S. Office Action dated Mar. 9, 2016 issued in U.S. Appl. No. 14/299,976.
U.S. Final Office Action dated Jul. 6, 2016 issued in U.S. Appl. No. 14/299,976.
U.S. Office Action dated Oct. 21, 2016 issued in U.S. Appl. No. 14/299,976.
U.S. Final Office Action dated Apr. 19, 2017 issued in U.S. Appl. No. 14/299,976.
U.S. Final Office Action dated Jun. 8, 2017 issued in U.S. Appl. No. 14/299,976.
U.S. Office Action dated Jan. 13, 2016 issued in U.S. Appl. No. 14/464,551.
U.S. Notice of Allowance dated Jun. 23, 2016 issued in U.S. Appl. No. 14/464,551.
U.S. Office Action dated Sep. 23, 2016 issued in U.S. Appl. No. 14/800,538.
U.S. Notice of Allowance dated Jan. 17, 2017 issued in U.S. Appl. No. 14/800,538.
U.S. Office Action dated Feb. 22, 2017 issued in U.S. Appl. No. 14/671,821.
U.S. Notice of Allowance dated Jul. 3, 2017 issued in U.S. Appl. No. 14/671,821.
U.S. Office Action dated Jun. 30, 2017 issued in U.S. Appl. No. 15/251,772.
U.S. Office Action dated Jun. 28, 2016 issued in U.S. Appl. No. 14/671,844.
U.S. Final Office Action dated Nov. 25, 2016 issued in U.S. Appl. No. 14/671,844.
U.S.Notice of Allowance dated Mar. 13, 2017 issued in U.S. Appl. No. 14/671,844.
U.S. Office Action dated Jan. 26, 2017 issued in U.S. Appl. No. 15/052,293.
U.S. Final Office Action dated May 2, 2017 issued in U.S. Appl. No. 15/052,293.
U.S. Notice of Allowance dated May 24, 2017 issued in U.S. Appl. No. 15/052,293.
U.S. Notice of Allowance [Supplemental Notice of Allowability] dated Jun. 20, 2017 issued in U.S. Appl. No. 15/052,293.
U.S. Office Action dated May 20, 2016 issued in U.S. Appl. No. 14/928,058.
U.S. Final Office Action dated Jan. 6, 2017 issued in U.S. Appl. No. 14/928,058.
U.S. Notice of Allowance dated Mar. 16, 2017 issued in U.S. Appl. No. 14/928,058.
U.S. Office Action dated Jun. 23, 2017 issued in U.S. Appl. No. 15/190,089.
U.S. Office Action dated Dec. 27, 2016 issued in U.S. Appl. No. 15/287,520.
U.S. Notice of Allowance dated Mar. 27, 2017 issued in U.S. Appl. No. 15/287,520.
PCT International Search Report dated May 27, 2011, issued in PCT/US2010/052701.
PCT International Preliminary issued Report on Patentability and Written Opinion dated Apr. 26, 2012, in PCT/US2010/052701.
Japanese Office Action dated Feb. 25, 2014 issued in JP 2012-534361.
PCT International Search Report and Written Opinion dated Sep. 3, 2015 issued in PCT/US2015/029732.
PCT International Preliminary Report on Patentability and Written Opinion dated Nov. 24, 2016 issued in PCT/US2015/029732.
PCT International Search Report and Written Opinion dated May 26, 2016 issued in PCT/US2016/019513.
PCT International Search Report and Written Opinion dated Apr. 14, 2016 issued in PCT/US2015/058370.
PCT International Preliminary issued Report on Patentability and Written Opinion dated May 11, 2017 in PCT/US2015/058370.
PCT International Search Report and Written Opinion dated Sep. 15, 2016 issued in PCT/US2016/029528.
PCT International Search Report and Written Opinion dated Sep. 29, 2016 issued in PCT/US2016/039089.
PCT International Search Report and Written Opinion dated Jan. 19, 2017 issued in PCT/US2016/055997.
"Electronic Foot Size Measuring Devices," *Sensatech Research LTD., Custom Electronic Sensing Solutions*, Registered Office: 4 Heath Square, Boltro Road, Haywards Heath, RH16 1BL Company Registration No. 4524018 Cardiff [retrieved at http:www.electronicsarena.co.uk/companies/sensatech-research/products/electronic-foot-size-measureing-devices on Sep. 17, 2015], 3 pages.
"iStep® Digital Foot Scan," (© 2002-2015) [retrieved at http://www.foot.com/site/iStep on Sep. 17, 2015], 1 page.
"Podotech Elftman," and Podotech Elftman Brochure (UK Version) [retrieved at http://www.podotech.com/diagnostics/podotech-elftman-2/ on Sep. 17, 2015] podo+tech®, Foot Care Technology Solutions, 7 pages.
Roh, Jung-Sim et al. (2011) "Robust and reliable fabric and piezoresistive multitouch sensing surfaces for musical controllers," from Alexander Refsum Jensenius, Recorded at: *11th International Conference on New Interfaces for Musical Expression* May 30-Jun. 1, 2011, Oslo, Norway, a vimeo download at http://vimeo.com/26906580.
"The Emed®-Systems," [retrieved at http://www.novel.de/novelcontent/emed on Sep. 17, 2015] novel.de, 4 pages.
U.S. Appl. No. 15/479,103, filed Apr. 4, 2017, McMillen et al.
U.S. Appl. No. 15/483,926, filed Apr. 10, 2017, McMillen.
U.S. Appl. No. 15/630,840, filed Jun. 22, 2017, McMillen et al.
U.S. Notice of Allowance dated Oct. 16, 2017 issued in U.S. Appl. No. 14/728,872.
U.S. Office Action dated Aug. 25, 2017 issued in U.S. Appl. No. 14/728,873.
U.S. Final Office Action dated Dec. 22, 2017 issued in U.S. Appl. No. 14/728,873.
U.S. Office Action dated Mar. 26, 2018 issued in U.S. Appl. No. 14/728,873.
U.S. Office Action dated Sep. 1, 2017 issued in U.S. Appl. No. 14/299,976.
U.S. Notice of Allowance dated Feb. 22, 2018 issued in U.S. Appl. No. 14/299,976.
U.S. Final Office Action dated Nov. 15, 2017 issued in U.S. Appl. No. 15/251,772.
U.S. Office Action dated Feb. 22, 2018 issued in U.S. Appl. No. 15/251,772.
U.S. Notice of Allowance dated Sep. 22, 2017 issued in U.S. Appl. No. 15/052,293.
U.S. Notice of Allowance [Supplemental Notice of Allowability] dated Oct. 19, 2017 issued in U.S. Appl. No. 15/052,293.
U.S. Office Action dated Nov. 3, 2017 issued in U.S. Appl. No. 15/138,802.
U.S. Final Office Action dated Mar. 1, 2018 issued in U.S. Appl. No. 15/138,802.
U.S. Advisory Action dated May 16, 2018 issued in U.S. Appl. No. 15/138,802.
U.S. Notice of Allowance dated Aug. 10, 2017 issued in U.S. Appl. No. 15/190,089.
PCT International Preliminary Report on Patentability and Written Opinion dated Sep. 8, 2017 issued in PCT/US2016/019513.
PCT International Preliminary Report on Patentability and Written Opinion dated Oct. 31, 2017 issued in PCT/US2016/029528.
PCT International Preliminary Report on Patentability and Written Opinion dated Dec. 26, 2017 issued in PCT/US2016/039089.
PCT International Preliminary Report on Patentability and Written Opinion dated Apr. 26, 2018 issued in PCT/US2016/055997.
PCT International Search Report and Written Opinion dated Aug. 14, 2017 issued in PCT/US2017/026812.
U.S. Appl. No. 15/835,131, filed Dec. 7, 2017, McMillen et al.
U.S. Appl. No. 15/986,649, filed May 22, 2018, McMillen et al.
U.S. Notice of Allowance dated Jul. 19, 2018 issued in U.S. Appl. No. 14/728,873.
U.S. Office Action dated Jul. 12, 2018 issued in U.S. Appl. No. 15/483,926.
U.S. Office Action dated Sep. 4, 2018 issued in U.S. Appl. No. 15/251,772.

(56) References Cited

OTHER PUBLICATIONS

U.S. Office Action dated Jul. 24, 2018 issued in U.S. Appl. No. 15/835,131.
U.S. Notice of Allowance dated Jul. 3, 2018 issued in U.S. Appl. No. 15/138,802.
U.S. Appl. No. 16/148,570, filed Oct. 1, 2018, McMillen et al.
U.S. Office Action dated Dec. 31, 2018 issued in U.S. Appl. No. 15/374,816.
U.S. Notice of Allowance dated Mar. 11, 2019 issued in U.S. Appl. No. 15/374,816.
U.S. Notice of Allowance dated Dec. 31, 2018 issued in U.S. Appl. No. 15/483,926.
U.S. Final Office Action dated Dec. 21, 2018 issued in U.S. Appl. No. 15/251,772.
U.S. Notice of Allowance dated Mar. 5, 2019 issued in U.S. Appl. No. 15/251,772.
U.S. Notice of Allowance dated Dec. 4, 2018 issued in U.S. Appl. No. 15/835,131.
U.S. Office Action dated Mar. 6, 2019 issued in U.S. Appl. No. 15/835,131.
U.S. Office Action dated Dec. 13, 2018 issued in U.S. Appl. No. 15/690,108.
Japanese Office Action dated Dec. 4, 2018 issued in JP 2016-566814.
PCT International Search Report and Written Opinion dated Nov. 8, 2018 issued in PCT/US2018/035848.
PCT International Preliminary Report on Patentability dated Nov. 1, 2018 issued in PCT/US2017/026812.
U.S. Appl. No. 16/362,017, filed Mar. 22, 2019, McMillen et al.

\* cited by examiner

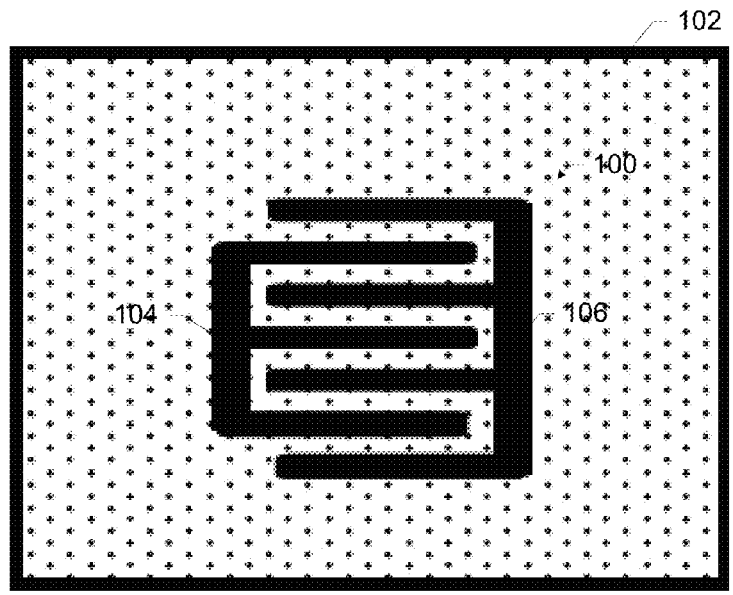
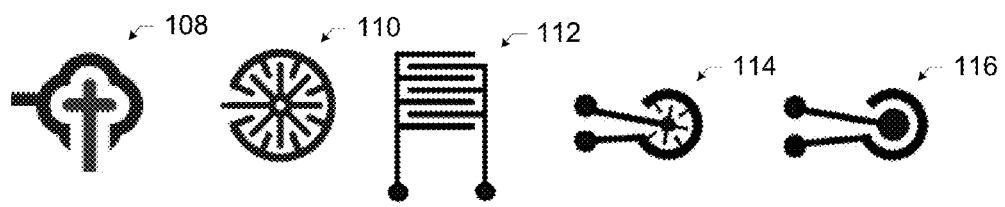
*FIG. 1*

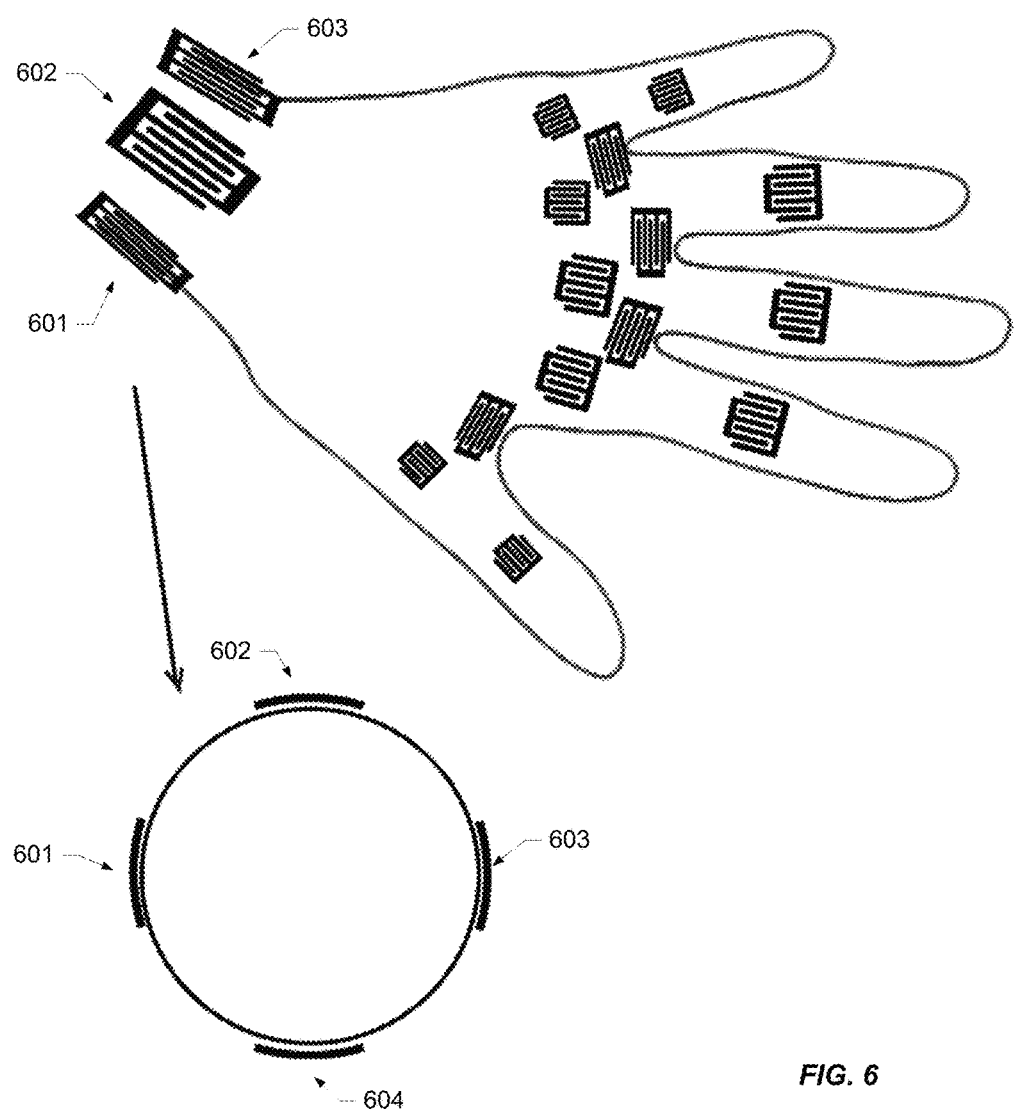
FIG. 6
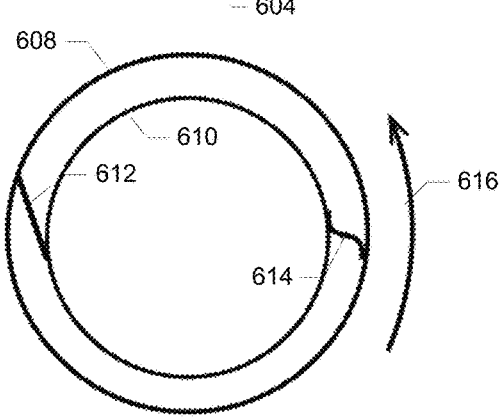

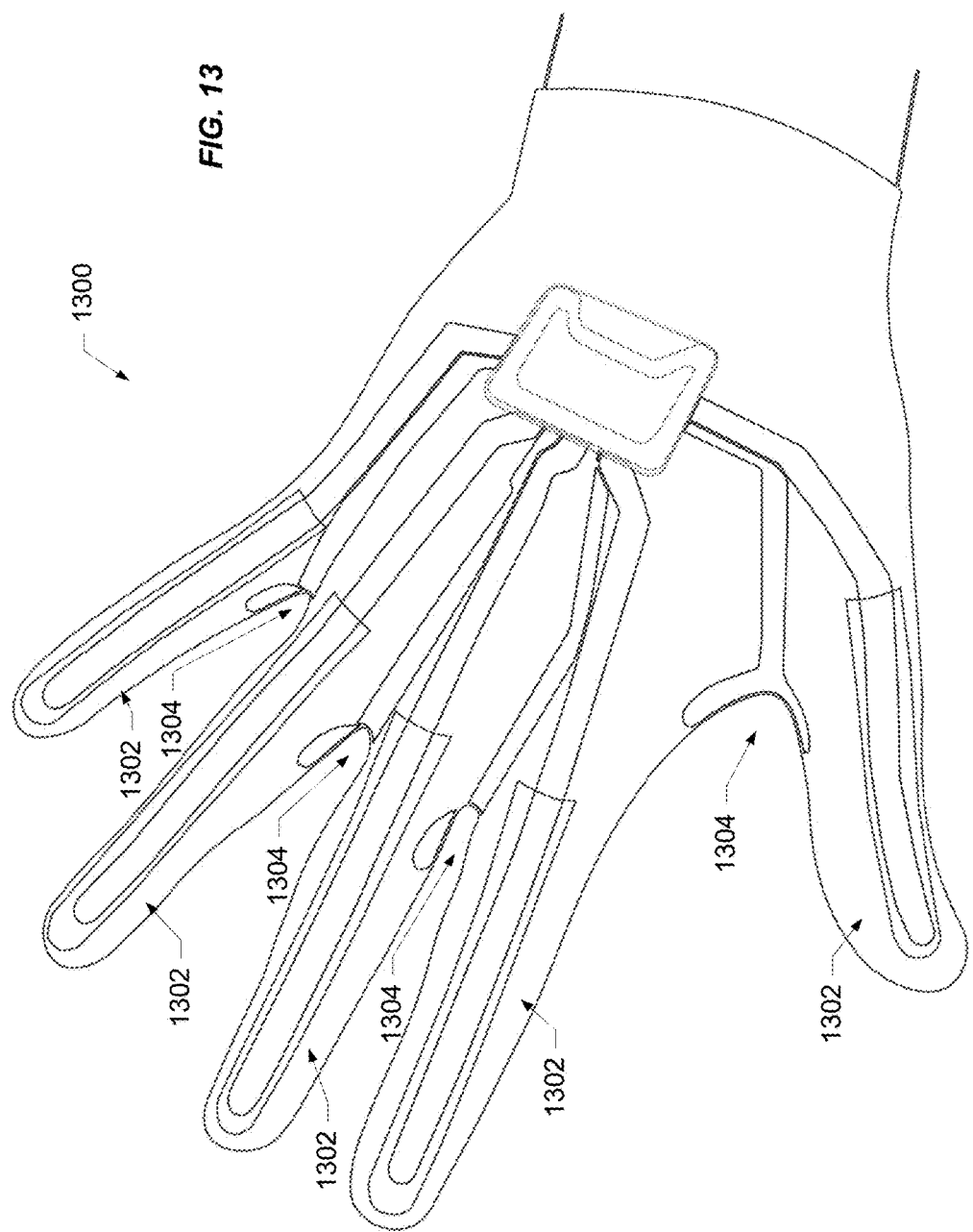

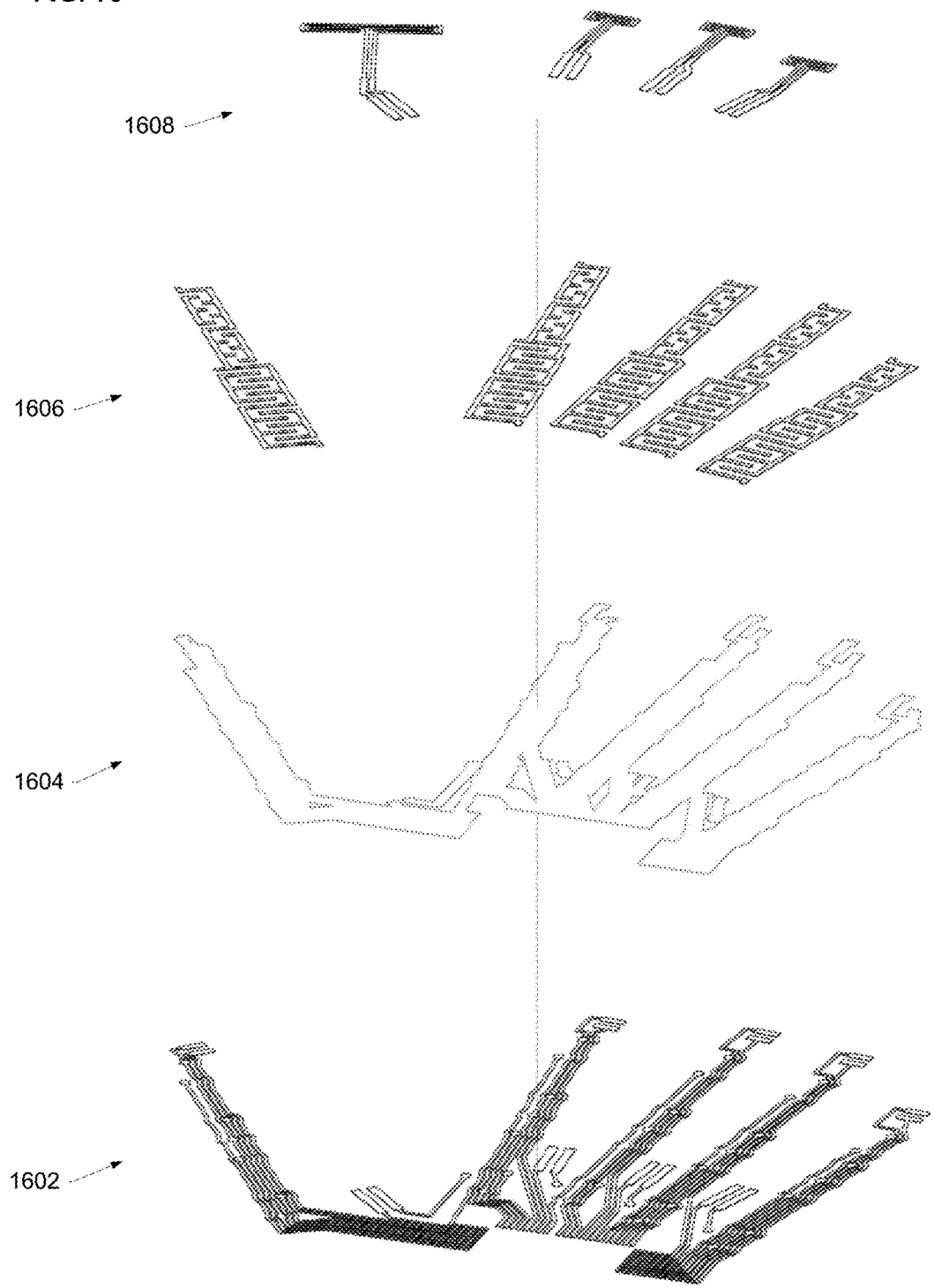

SENSOR SYSTEM INTEGRATED WITH A GLOVE

RELATED APPLICATION DATA

The present application is a continuation-in-part of and claims priority under 35 U.S.C. 120 to U.S. patent application Ser. No. 14/928,058 entitled Sensor System Integrated with a Glove filed on Oct. 30, 2015, which is a non-provisional of and claims priority under 35 U.S.C. 119(e) to U.S. Provisional Patent Application No. 62/072,798 entitled Flexible Sensors and Applications filed on Oct. 30, 2014. U.S. patent application Ser. No. 14/928,058 is also a continuation-in-part of and claims priority under 35 U.S.C. 120 to U.S. patent application Ser. No. 14/671,821 entitled Flexible Sensors and Applications filed on Mar. 27, 2015, which is a continuation-in-part of and claims priority under 35 U.S.C. 120 to U.S. patent application Ser. No. 14/299,976 entitled Piezoresistive Sensors and Applications filed Jun. 9, 2014. The entire disclosure of each of the foregoing applications is incorporated herein by reference for all purposes.

BACKGROUND

Demand is rapidly rising for technologies that bridge the gap between computing devices and the physical world. These interfaces typically require some form of sensor technology that translates information from the physical domain to the digital domain. The "Internet of Things" contemplates the use of sensors in a virtually limitless range of applications, for many of which conventional sensor technology is not well suited.

SUMMARY

According to various implementations, sensors and applications of sensors are provided. According to some implementations, a sensor system includes a flexible substrate for alignment or integration with a portion of a glove. A plurality of conductive trace groups formed directly on the substrate at sensor locations correspond to at least some finger joints of a human hand. Each of the conductive trace groups includes two or more conductive traces. The resistance between the conductive traces in each of the conductive trace groups varies with force on piezoresistive material in contact with the conductive trace group. Circuitry is configured to receive a signal from each of the conductive trace groups and generate control information in response thereto. The control information represents the force on the piezoresistive material in contact with each of the conductive trace groups.

According to a particular class of implementations, the flexible substrate is a dielectric material, and the piezoresistive material is a plurality of patches. Each patch of piezoresistive material is in contact with a corresponding one of the conductive trace groups at the sensor locations. According to a more specific implementation, the dielectric material is a thermoplastic material, and the sensor system includes a second flexible substrate of the thermoplastic material. The flexible substrate on which the conductive trace groups are formed, the patches of piezoresistive material, and the second flexible substrate are thermally bonded together such that the patches of piezoresistive material are secured in contact with the corresponding conductive trace groups.

According to another class of implementations, the flexible substrate is the piezoresistive material which may be, for example, a piezoresistive fabric.

A further understanding of the nature and advantages of various implementations may be realized by reference to the remaining portions of the specification and the drawings.

BRIEF DESCRIPTION OF THE DRAWINGS

FIG. 1 shows examples of trace patterns that may be integrated with a flexible substrate.

FIG. 6 shows another implementation of a sensor array.

FIGS. 12-14C show another implementation of a sensor system.

FIGS. 15 and 16 show another implementation of a sensor system.

DETAILED DESCRIPTION

Figure 2:
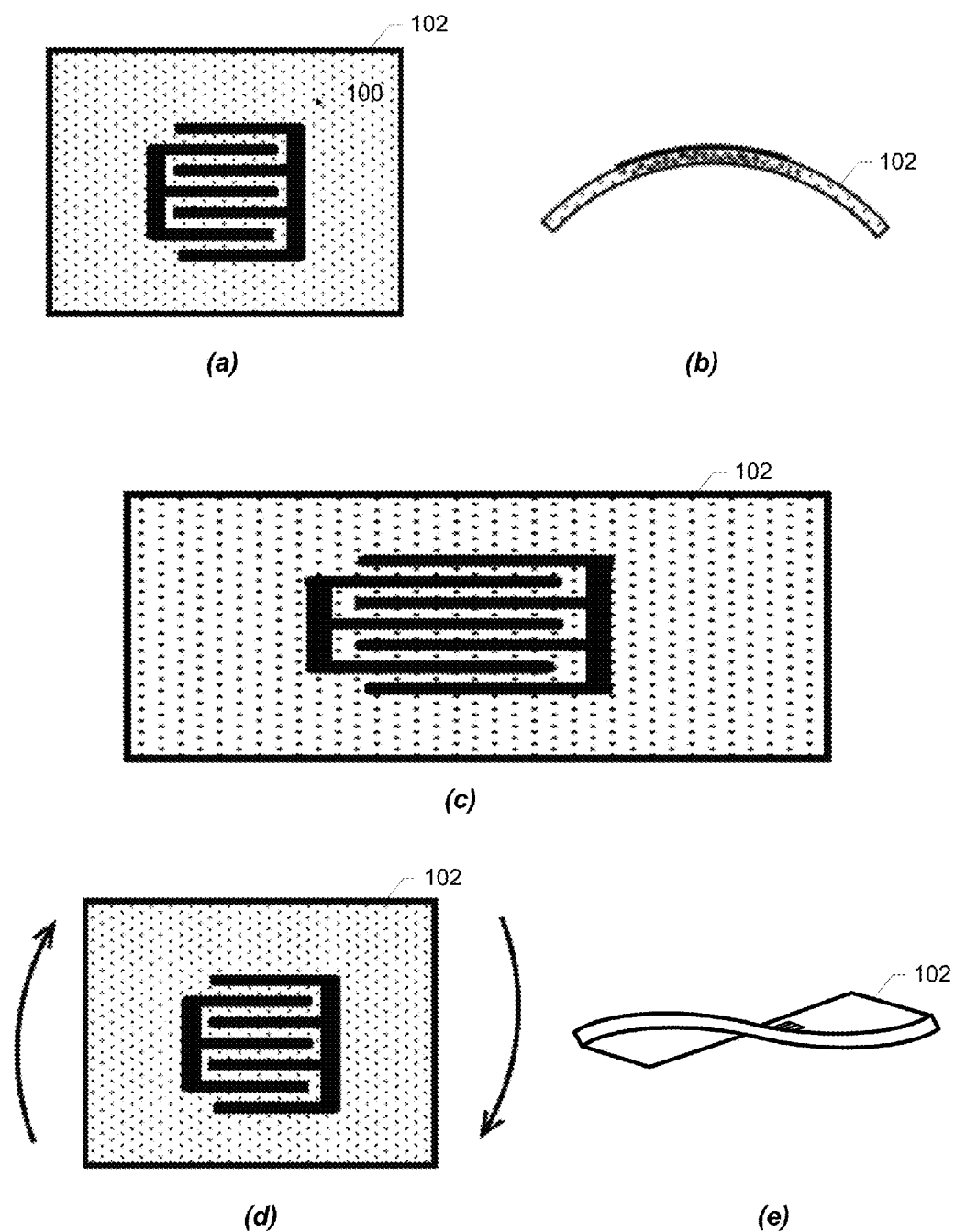
FIG. 2 shows examples of different types of distortions to a flexible substrate.

Sensors and sensor systems incorporating piezoresistive materials are described in this disclosure. In particular, sensor systems for integration with gloves for the human hand are described. Specific implementations are described herein including the best modes contemplated. Examples of these implementations are illustrated in the accompanying drawings. However, the scope of this disclosure is not limited to the described implementations. Rather, this disclosure is intended to cover alternatives, modifications, and equivalents of these implementations. In the following description, specific details are set forth in order to provide a thorough understanding of the described implementations. Some implementations may be practiced without some or all of these specific details. In addition, well known features may not have been described in detail to promote clarity.

Piezoresistive materials include any of a class of materials that exhibit a change in electrical resistance in response to mechanical force or pressure applied to the material. One class of sensor systems described herein includes conductive traces formed directly on or otherwise integrated with a flexible substrate of piezoresistive material, e.g., a piezoresistive fabric or other flexible material. Another class of sensor systems described herein includes conductive traces formed directly on or otherwise integrated with a flexible dielectric substrate with flexible piezoresistive material that is tightly integrated with the dielectric substrate and in contact with portions of the traces. When force or pressure is applied to such a sensor system, the resistance between traces connected by the piezoresistive material changes in a time-varying manner that is representative of the applied force. A signal representative of the magnitude of the applied force is generated based on the change in resistance. This signal is captured via the conductive traces (e.g., as a voltage or a current), digitized (e.g., via an analog-to-digital converter), processed (e.g., by an associated processor, controller, or suitable control circuitry), and mapped (e.g., by the associated processor, controller, or control circuitry) to a control function that may be used in conjunction with virtually any type of process, device, or system. The output signals from such sensor systems may also be used to detect a variety of distortions and/or deformations of the substrate(s) on which they are formed or with which they are integrated such as, for example, bends, stretches, torsions, rotations, etc.

Printing, screening, depositing, or otherwise forming conductive traces directly onto flexible substrates allows for the creation of a sensor or sensor array that fits any arbitrary shape or volume. The piezoresistive material on which the traces are formed or with which the traces are in contact may be any of a variety of woven and non-woven fabrics having piezoresistive properties. Implementations are also contemplated in which the piezoresistive material may be any of a variety of flexible, stretchable, or otherwise deformable materials (e.g., rubber, or a stretchable fabric such as spandex or open mesh fabrics) having piezoresistive properties. The conductive traces may be formed on the piezoresistive material or a flexible dielectric substrate using any of a variety of conductive inks or paints. Implementations are also contemplated in which the conductive traces are formed using any flexible conductive material that may be formed on a flexible substrate. It should therefore be understood that, while specific implementations are described with reference to specific materials and techniques, the scope of this disclosure is not so limited.

Both one-sided and two-side implementations are contemplated, e.g., conductive traces can be printed on one or both sides of flexible substrate. As will be understood, two-sided implementations may require some mechanism for connecting conductive traces on one side of the substrate to those on the other side. Some implementations use vias in which conductive ink or paint is flowed through the vias to establish the connections. Alternatively, metal vias or rivets may make connections through the flexible substrate.

Both single and double-sided implementations may use insulating materials formed over conductive traces. This allows for the stacking or layering of conductive traces and signal lines, e.g., to allow the routing of signal line to isolated structures in a manner analogous to the different layers of a printed circuit board.

Routing of signals on and off the flexible substrate may be achieved in a variety of ways. A particular class of implementations uses elastomeric connectors (e.g., ZEBRA® connectors) which alternate conductive and non-conductive rubber at a density typically an order of magnitude greater than the width of the conductive traces to which they connect (e.g., at the edge of the substrate). Alternatively, a circuit board (possibly made of a flexible material such as Kapton), or a bundle of conductors may be riveted to the substrate. The use of rivets may also provide mechanical reinforcement to the connection.

Matching conductive traces or pads on both the flexible substrate and a circuit board can be made to face each. A layer of conductive adhesive (e.g., a conductive epoxy such as Masterbond EP79 from Masterbond, Inc. of Hackensack, N.J.) can be applied to one of the surfaces and then mated to the other surface. The conductive traces or pads can also be held together with additional mechanical elements such as a plastic sonic weld or rivets. If conductive rivets are used to make the electrical connections to the conductive traces of the flexible substrate, the conductive adhesive may not be required. Conductive threads may also be used to connect the conductive traces of the flexible substrate to an external assembly.

According to a particular class of implementations, the piezoresistive material is a pressure sensitive fabric manufactured by Eeonyx, Inc., of Pinole, Calif. The fabric includes conductive particles that are polymerized to keep them suspended in the fabric. The base material is a polyester felt selected for uniformity in density and thickness as this promotes greater uniformity in conductivity of the finished piezoresistive fabric. That is, the mechanical uniformity of the base material results in a more even distribution of conductive particles when the slurry containing the conductive particles is introduced. The fabric may be woven. Alternatively, the fabric may be non-woven such as, for example, a calendared fabric e.g., fibers, bonded together by chemical, mechanical, heat or solvent treatment. For implementations in which conductive traces are formed on the piezoresistive fabric, calendared material presents a smoother outer surface which promotes more accurate screening of conductive inks than a non-calendared material.

The conductive particles in the fabric may be any of a wide variety of materials including, for example, silver, copper, gold, aluminum, carbon, etc. Some implementations may employ carbon graphenes that are formed to grip the fabric. Such materials may be fabricated using techniques described in U.S. Pat. No. 7,468,332 for Electroconductive Woven and Non-Woven Fabric issued on Dec. 23, 2008, the entire disclosure of which is incorporated herein by reference for all purposes. However, it should again be noted that any flexible material that exhibits a change in resistance or conductivity when force or pressure is applied to the material will be suitable for implementation of sensors as described herein.

According to a particular class of implementations, conductive traces having varying levels of conductivity are formed on flexible piezoresistive material or an adjacent flexible dielectric substrate using conductive silicone-based inks manufactured by, for example, E.I. du Pont de Nemours and Company (DuPont) of Wilmington, Del., and/or Creative Materials of Ayer, Mass. An example of a conductive ink suitable for implementing highly conductive traces for use with various implementations is product number 125-19 from Creative Materials, a flexible, high temperature, electrically conductive ink. Examples of conductive inks for implementing lower conductivity traces for use with various implementations are product numbers 7102 and 7105 from DuPont, both carbon conductive compositions. Examples of dielectric materials suitable for implementing insulators for use with various implementations are product numbers 5018 and 5036 from DuPont, a UV curable dielectric and an encapsulant, respectively. These inks are flexible and durable and can handle creasing, washing, etc. The degree of conductivity for different traces and applications is controlled by the amount or concentration of conductive particles (e.g., silver, copper, aluminum, carbon, etc.) suspended in the silicone. These inks can be screen printed or printed from an inkjet printer. Another class of implementations uses conductive paints (e.g., carbon particles mixed with paint) such as those that are commonly used for EMI shielding and ESD protection.

Examples of sensors and arrays of sensors that may be used with various implementations enabled by the present disclosure are described in U.S. patent application Ser. No. 14/299,976 entitled Piezoresistive Sensors and Applications filed on Jun. 9, 2014, the entire disclosure of which is incorporated herein by reference for all purposes. However, it should be noted that implementations are contemplated that employ a variety of other suitable sensor technologies.

Forming sensors on flexible substrates enables numerous useful devices. Many of these devices employ such sensors to detect the occurrence of touch events, the force or pressure of touch events, the duration of touch events, the location of touch events, the direction of touch events, and/or the speed of motion of touch events. The output signals from such sensors may also be used to detect a variety of distortions and/or deformations of the substrate on which they are formed or with which they are integrated such as, for example, bends, stretches, torsions, rotations, etc. The information derived from such sensors may be used to effect a wide variety of controls and/or effects. Examples of distortions and/or deformations are described below with reference to the accompanying figures. As will be understood, the specific details described are merely examples for the purpose of illustrating the range of techniques enabled by this disclosure.

FIG. 1 shows an example of a sensor trace pattern 100 integrated with a flexible substrate 102. The flexible substrate may be a piezoresistive material or a dielectric material. In the latter case, a flexible piezoresistive material is tightly integrated with the dielectric material an in contact with the sensor trace pattern. Trace pattern 100 includes a pair of conductive traces, one of which (trace 104) provides a sensor signal to associated circuitry (not shown), and the other of which (trace 106) is connected to ground or a suitable reference. Some representative examples of other trace patterns 108-116 are shown. In some implementations, the traces of a trace pattern may be formed directly, e.g., by screening or printing, on the flexible substrate which might be, for example, a piezoresistive fabric. However, it should be noted that, among other things, the geometries of the sensor trace pattern(s), the number of traces associated with each sensor, the number, spacing, or arrangement of the sensors, the relationship of the sensors to the substrate, the number of layers or substrates, and the nature of the substrate(s) may vary considerably from application to application, and that the depicted configurations are merely examples for illustrative purposes.

FIG. 2 shows examples of different types of distortions to flexible substrate 102 that may be detected via sensor trace pattern 100. FIG. 2(a) shows substrate 102 in its non-distorted state. FIG. 2(b) shows a side view of substrate 102 bending; FIG. 2(c) shows substrate 102 stretching; FIG. 2(d) represents substrate 102 rotating relative to surrounding material; and FIG. 2(e) shows a side view of substrate 102 twisting due to an applied torque (i.e., torsion). In each of these scenarios, the resistance of the piezoresistive material in contact with trace pattern 100 changes in response to the applied force (e.g., goes down or up due to compression or increased separation of conductive particles in the piezoresistive material). This change (including its magnitude and time-varying nature) is detectable via sensor trace pattern 100 and associated electronics (not shown).

Figure 3:
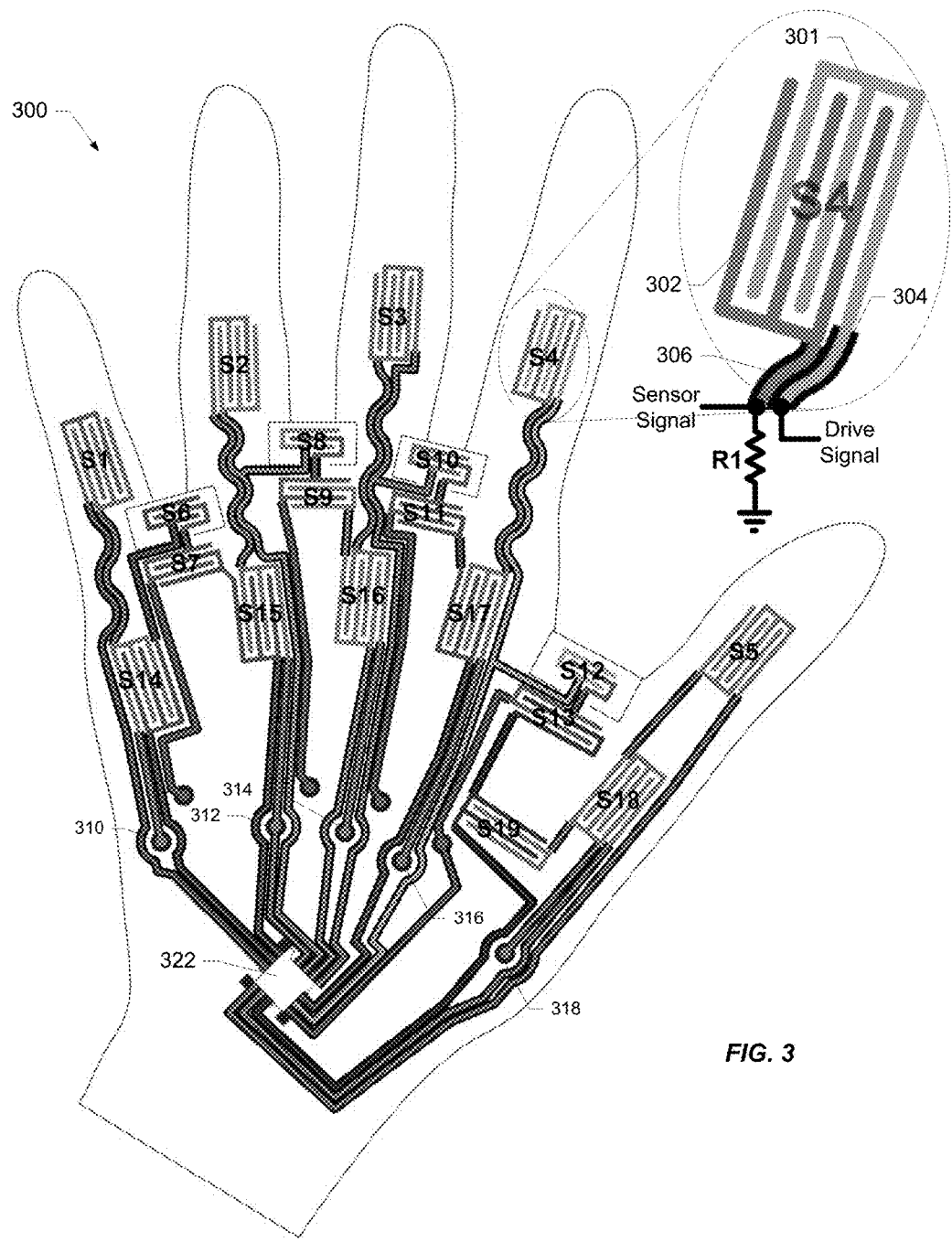
FIG. 3 shows a particular implementation of a sensor array.

According to a particular implementation illustrated in FIG. 3, sensor trace patterns are formed on the stretchable material of a sensor glove 300 that may be used, for example, to translate a human's hand motions and the hand's interactions with the physical world into a virtual representation of the hand (or some other virtual object) and its interactions in a virtual environment. In another example, the hand's motions and interactions may be used to control a robotic hand or device in the physical world. The material on which the trace patterns are formed may be a flexible piezoresistive material or a flexible dielectric material. Again, in the latter case, a flexible piezoresistive material is tightly integrated with the flexible substrate on which the trace patterns are formed and in contact with the trace patterns at the various sensor locations (i.e., S1-S19).

As shown, trace patterns corresponding to some of the sensors (e.g., S1-S5 and S14-S18) are placed to coincide with various joints of the fingers (e.g., knuckles or finger joints) to capture distortion and/or deformation of the glove in response to bending and flexing of those joints. Other sensors (e.g., S6-S13 and S19) are placed to capture stretching of the glove, e.g., as occurs when the fingers of the hand are spread out. Other sensors (not shown) may also be placed on the palm of the glove and/or the tips of the fingers to detect bending and flexing forces as well as forces relating, for example, to touching, gripping, or otherwise coming into contact with objects or surfaces.

Portions of the conductive traces that are not intended to be part of a sensor (e.g., signal routing traces) may be shielded or insulated to reduce any unwanted contributions to the sensor signals. That is, the portions of the conductive traces that bring the drive and sense signals to and from the sensors may be insulated from the piezoresistive material using, for example, a dielectric or non-conducting material between the piezoresistive material and the conductive traces. According to some implementations in which the conductive traces are formed on a flexible dielectric material, isolated pieces of piezoresistive material may be selectively located at the respective sensor locations.

In the depicted implementation there are 19 sensors, S1-S19. Each of the sensors includes two adjacent traces, the respective patterns of which include extensions that alternate. See, for example, the magnified view of sensor S4. One of the traces 301 receives a drive signal; the other trace 302 transmits the sensor signal to associated sensor circuitry (not shown). The drive signal might be provided, for example, by connecting the trace (permanently or temporarily) to a voltage reference, a signal source that may include additional information in the drive signal, a GPIO (General Purpose Input Output) pin of an associated processor or controller, etc. And as shown in the example in FIG. 3, the sensor signal might be generated using a voltage divider in which one of the resistors of the divider includes the resistance between the two traces through the intervening piezoresistive material. The other resistor (represented by R1) might be included, for example, with the associated sensor circuitry. As the resistance of the piezoresistive material changes with applied force or pressure, the sensor signal also varies as a divided portion of the drive signal.

The sensors are energized (via the drive signals) and interrogated (via the sensor signals) to generate an output signal for each that is a representation of the force exerted on that sensor. As will also be appreciated, and depending on the application, implementations are contemplated having more or fewer sensors.

According to various implementations, different sets of sensors may be selectively energized and interrogated thereby reducing the number and overall area of traces on the substrate, as well as the required connections to sensor circuitry on an associated PCB (which may be positioned, for example, in cutout 322). For example, in the sensor system of FIG. 3, the 19 sensors are driven via 11 drive signal outputs from the sensor circuitry (not shown), and the sensor signals are received via 2 sensor signal inputs to the sensor circuitry; with 13 connections between the flexible substrate on which the conductive traces are formed and the PCB in cutout 322 as shown. The set of sensors providing sensor signals to one of the 2 sensor signal inputs (e.g., S6-S13 in one set and S1-S5 and S14-S19 in the other) may be energized in any suitable sequence or pattern such that any signal received on the corresponding sensor signal input can be correlated with the corresponding sensor drive signal by the sensor circuitry.

And because the sensor signals in this implementation are received by the sensor circuitry via two different sensor signal inputs, two sensors can be simultaneously energized as long as they are connected to different sensor signal inputs to the sensor circuitry. This allows for the sharing of drive signal lines. For example, in the implementation of FIG. 3, eight pairs of sensors share a common drive signal line, i.e., S2 and S8, S3 and S10, S4 and S12, S6 and S14, S7 and S15, S9 and S16, S11 and S17, and S13 and S19. The sharing of the common drive signal lines may be enabled by insulators which allow the conductive traces to cross, as well as locations at which the conductive traces simply diverge. Other suitable variations on this theme will be understood by those of skill in the art to be within the scope of this disclosure.

According to some implementations, a PCB may be connected to the conductive traces of the sensor array as described U.S. patent application Ser. No. 14/671,821 entitled Flexible Sensors and Applications filed on Mar. 27, 2015, the entire disclosure of which is incorporated herein by reference for all purposes. According to other implementations, any of a variety of techniques may be employed to make such a connection including, for example, elastomeric connectors (e.g., ZEBRA® connectors) which alternate conductive and non-conductive rubber at a density typically an order of magnitude greater than the width of the conductive traces to which they connect (e.g., at the edge of the fabric). A variety of other suitable alternatives are available to those of skill in the art.

Figure 4:
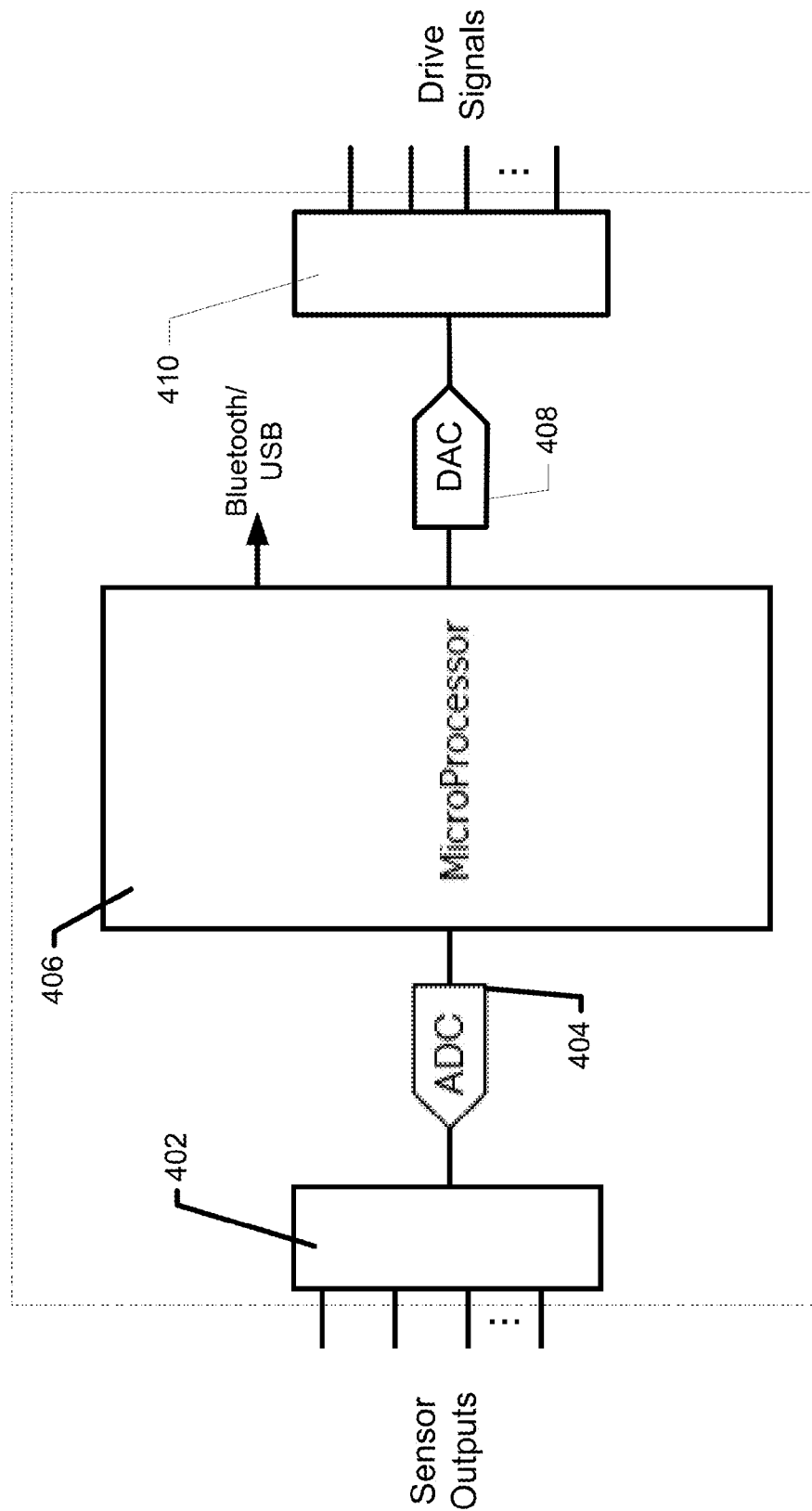
FIG. 4 is a simplified block diagram of sensor circuitry suitable for use with various implementations.

FIG. 4 is a simplified diagram of sensor circuitry that may be provided on a PCB for use with implementations described herein. For example, in the implementation described above with reference to FIG. 3, such sensor circuitry could be provided on a PCB in cutout 322 and connected to the conductive traces associated with sensors S1-S19. When force is applied to one of the sensors, a resulting signal (captured via the corresponding traces) is received and digitized (e.g., via multiplexer 402 and A-D converter 404) and may be processed locally (e.g., by processor 406) and/or transmitted to a connected device (e.g., via a Bluetooth or other wireless connection, or even via a USB connection). The sensors may be selectively energized by the sensor circuitry (e.g., under the control of processor 406 via D-A converter 408 and multiplexer 410) to effect the generation of the sensor signals. The C8051F380-GM controller (provided by Silicon Labs of Austin, Tex.) is an example of a processor suitable for use with various implementations.

In addition to transmission of data to and from a connected device, power may be provided to the sensor circuitry via a USB connection. Alternatively, systems that transmit data wirelessly (e.g., via Bluetooth) may provide power to the sensor circuitry using any of a variety of mechanisms and techniques including, for example, using one or more batteries, solar cells, and/or mechanisms that harvest mechanical energy. The LTC3588 (provided by Linear Technology Corporation of Milpitas, Calif.) is an example of an energy harvesting power supply that may be used with at least some of these diverse energy sources. Other suitable variations will be appreciated by those of skill in the art. And as will be appreciated, the sensor circuitry shown in FIG. 4 is merely an example. A wide range of sensor circuitry components, configurations, and functionalities are contemplated.

Figure 5:
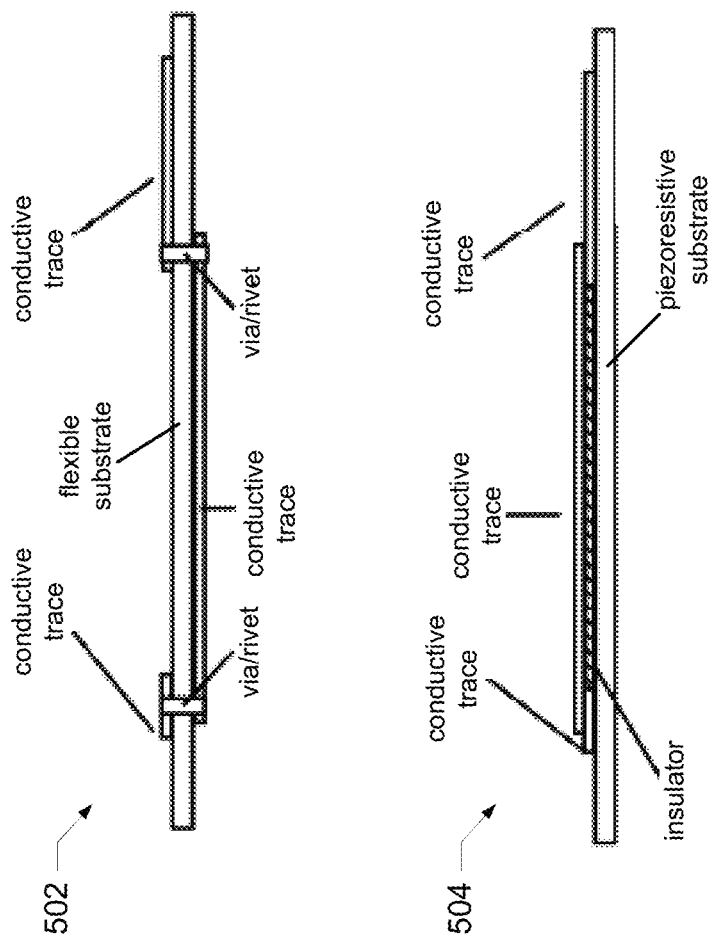
FIG. 5 shows examples of relationships among a piezoresistive substrate, conductive traces, and other conductive elements in one-sided and two-sided sensor implementations.

Both one-sided and two-side implementations are contemplated, e.g., conductive traces can be formed on one or both sides of a flexible substrate. As will be understood, two-sided implementations may require some mechanism for connecting conductive traces on one side of the substrate to those on the other side. Some implementations use vias in which conductive ink or paint is flowed through the vias to establish the connections. Alternatively or additionally, metal vias or rivets may make connections through the substrate. FIG. 5 illustrates the use of vias or rivets through the flexible substrate (e.g., configuration 502), and the use of insulating materials to insulate conductive traces from the substrate where the substrate is a piezoresistive material (e.g., configuration 504). Such mechanisms enable complex patterns of traces and routing of signals in a manner analogous to the different layers of a PCB.

For example, assuming an implementation in which the conductive traces are formed on piezoresistive material and referring again to FIG. 3, conductive traces that transmit signals to and from the sensors of glove 300 may be insulated from the underlying piezoresistive substrate by an insulating material. This is most clearly illustrated in the figure by insulators 304 and 306 that are associated with the drive and sense signal lines connected to sensor S4. In addition, sense signal lines from multiple sensors are connected to each other on the opposite side (not shown) of the material depicted in FIG. 3 through the use of vias at locations 310-318.

According to a particular implementation of a sensor glove and as shown in FIG. 6, sensor trace patterns (e.g., 601-604) may be placed in a roughly cylindrical configuration around the wrist to detect bending of the wrist in two dimensions (e.g., up, down, left, right). When all four sensors register a similar response, this could mean that the wrist is twisting. However, this configuration may not provide sufficient information to determine the direction of the twist. Therefore, according to a particular implementation, an outer cylinder 608 may be attached to an inner cylinder 610 with at least two stretch sensors (e.g., 612 and 614). By comparison of the outputs of these stretch sensors, the direction (e.g., 616) as well as the amount of the rotation can be captured.

Figure 7:
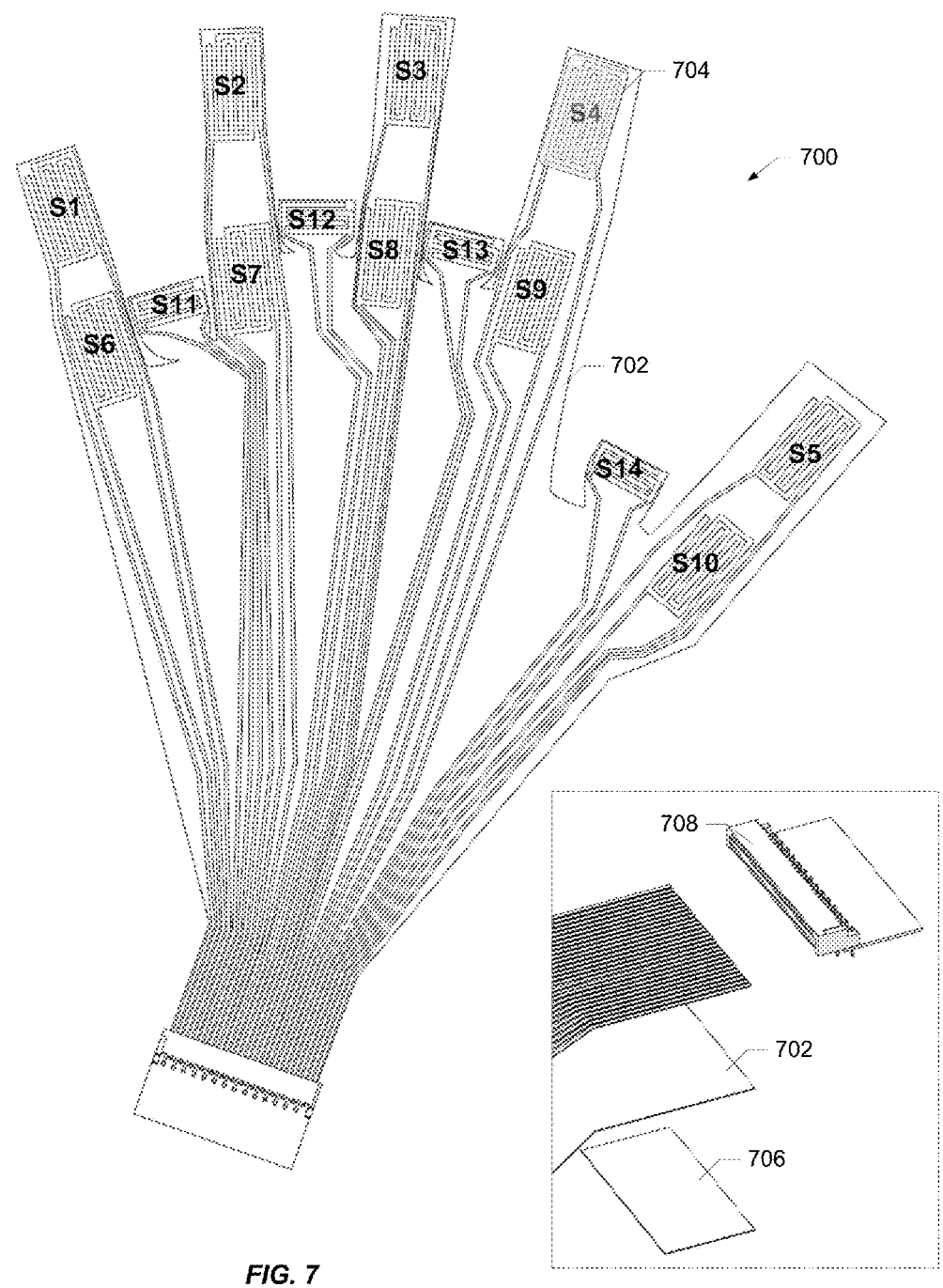
FIG. 7 shows another implementation of a sensor array.

FIG. 7 illustrates particular class of implementations of a sensor array 700 for use in a sensor glove in which conductive traces are formed on a flexible dielectric substrate 702. Operation of sensor array 700 is similar to operation of the sensor array of sensor glove 300 as described above. And it should be noted that the depicted configuration of traces might also be included in implementations in which the traces are formed on piezoresistive material.

According to a particular implementation, substrate 702 may be constructed from a thermoplastic polyurethane (TPU) material such as, for example, Products 3415 or 3914 from Bemis Associates Inc. of Shirley, Mass. The conductive traces may be screen printed on the substrate using a conductive flexible ink such as, for example, conductive silicone-based inks manufactured by E.I. du Pont de Nemours and Company (DuPont) of Wilmington, Del., or Creative Materials of Ayer, Mass. Patches of a piezoresistive material (e.g., the Eeonyx fabric discussed above) are placed in contact with the conductive traces at the locations of sensors S1-S14. See for example, piezoresistive patch 704 at sensor S4. A second substrate of the TPU material (not shown) is placed over array 700, and the assembly is heated to thermally bond the components together, fixing the piezoresistive patches in contact with their respective sensor traces.

Figure 8:
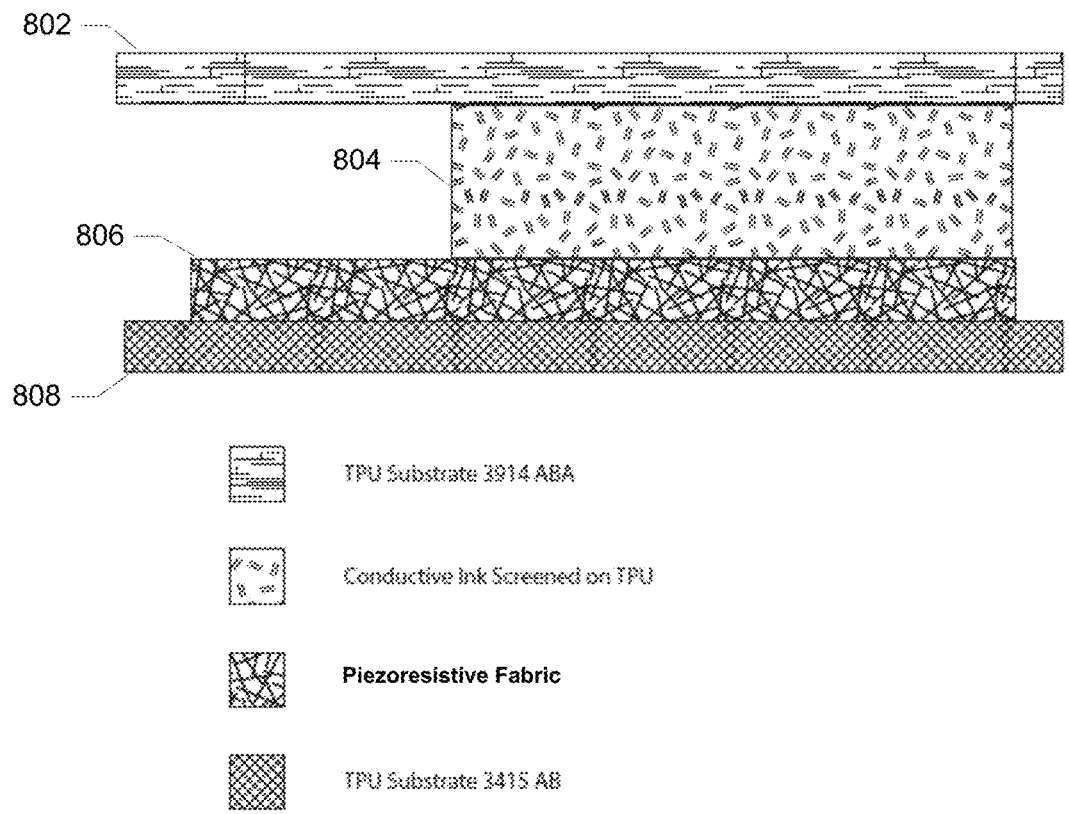
FIG. 8 shows an example of a cross-section of some of the components of a sensor system.
Figure 9:
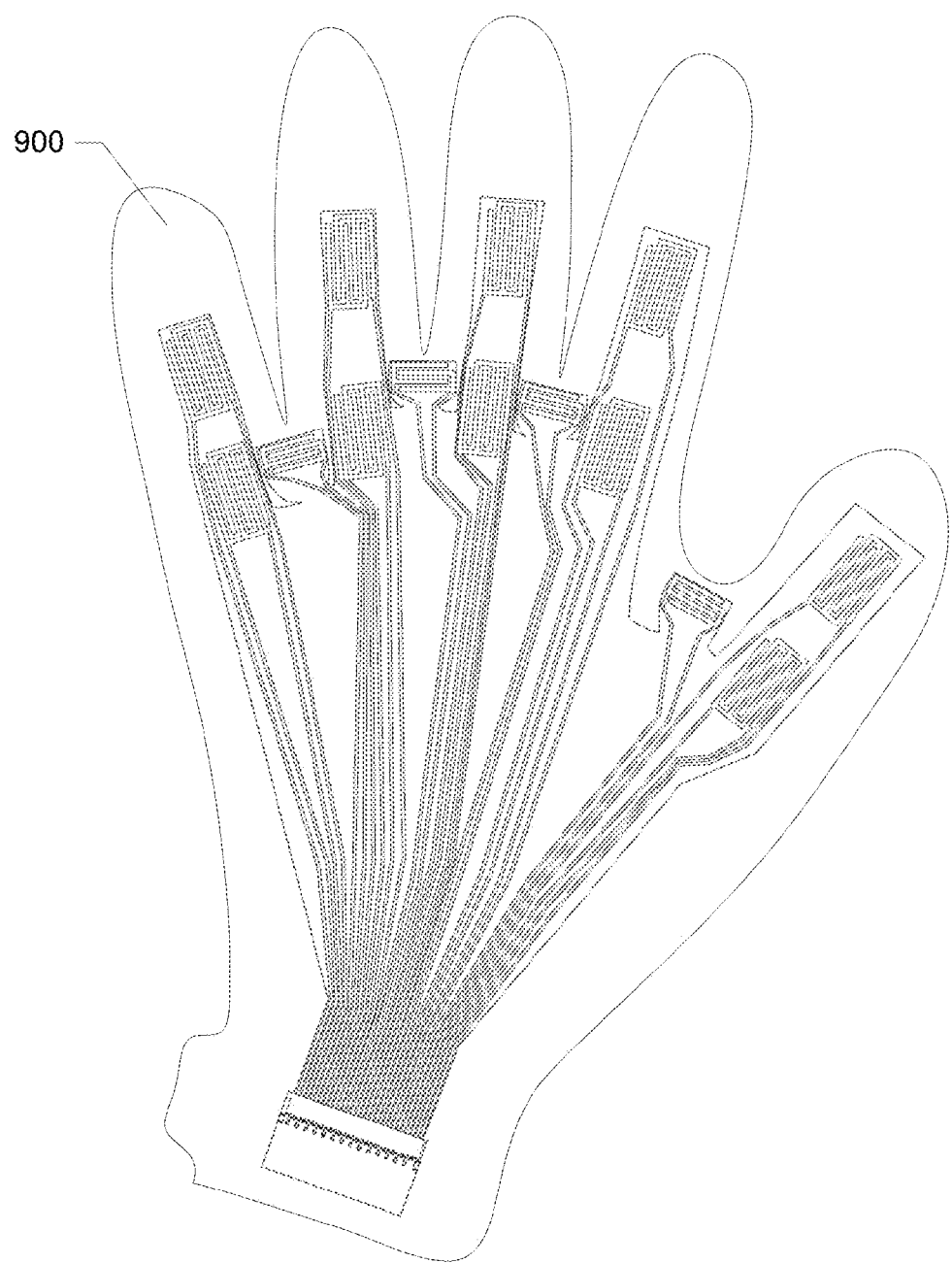
FIG. 9 shows an example of a sensor array integrated with a glove blank.

The relationships of the components of this assembly may be understood with reference to FIG. 8 which shows a flexible substrate 802 on which a conductive trace 804 is formed. Piezoresistive material 806 is maintained in contact with trace 804 by a second flexible substrate 808. In the depicted example, substrates 802 and 808 are TPU substrates and trace 804 is a conductive ink that is screen printed on TPU substrate 802. According to a particular implementation, TPU substrate 802 has an adhesive-barrier-adhesive (ABA) structure that allows for the assembly to be thermally bonded (e.g., melted) to another substrate such as, for example, a fabric glove blank 900 as depicted in FIG. 9. The other TPU substrate 808 is shown an adhesive-barrier (AB) structure so that it only bonds to the assembly. However, implementations are contemplated in which this substrate has an ABA structure to enable thermal bonding on both sides of the assembly.

According to a more specific implementation, stiffeners (not shown) may be placed in alignment with at least some of the piezoresistive patches and the corresponding trace patterns for the purpose of amplifying the signals generated by the corresponding sensors, e.g., by the force of the stiffener resisting bending of a knuckle and compressing the piezoresistive material. A stiffener might be a plastic film (e.g., polyethylene terephthalate or PET). Alternatively, a stiffener may be another piece of fabric. As yet another alternative, a stiffening material such as DuPont 5036 Dielectric ink may be silk-screened or printed on one of the components of the stack. As will be appreciated, stiffeners may be inserted at any point in the stack of materials (e.g., as depicted in FIG. 8) as long as the electrical connection between the conductive traces and the piezoresistive material is not unduly degraded.

Referring back to FIG. 7, a stiffener 706 (e.g., of PET or other suitable material) may be adhered to substrate 702 near the terminations of the conductive traces to allow for the insertion of the assembly into a connector 708 (see the exploded view in the lower right hand corner of the drawing). As will be appreciated, with stiffener 706 and the appropriate conductor spacing, this configuration allows for connection of sensor array 700 to any of a wide variety of industry standard connectors. According to a particular implementation, connector 708 is a Molex ZIF flat flex connector such as, for example, the Molex connector 52207-2860 (a 28 position connector) or the Molex connector 0522710869 (an 8 position connector as shown in FIG. 11).

Figure 10:
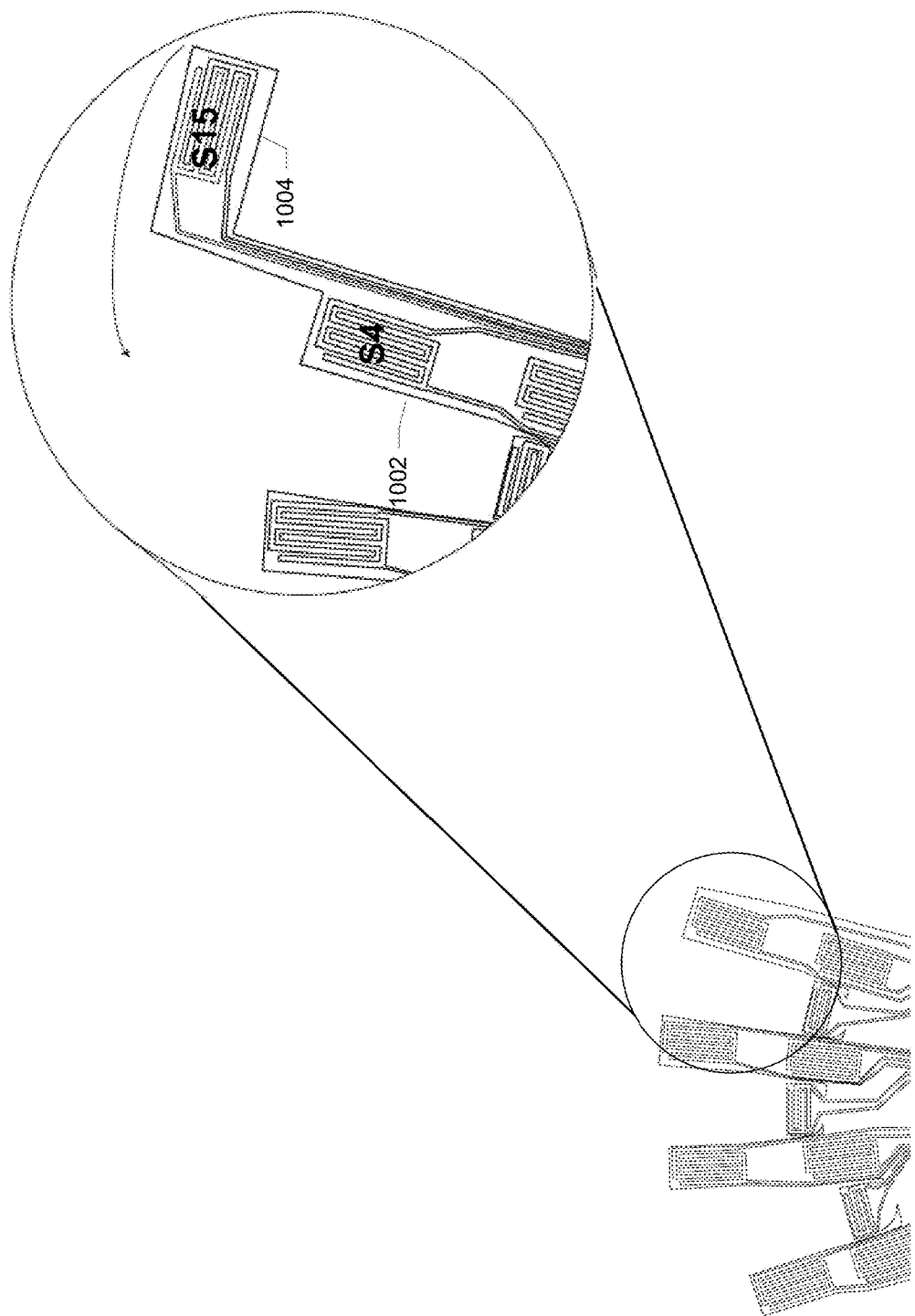
FIG. 10 shows another implementation of a sensor array.

As discussed above, sensor glove implementations are contemplated in which sensors are placed on the palm of the glove and/or the tips of the fingers to detect, for example, touching, gripping, or otherwise coming into contact with objects or surfaces. An example of how such a sensor might be integrated with an array is shown in FIG. 10. In the depicted example, flexible substrate 1002 extends beyond sensor S4 and includes a tab 1004 on which the conductive traces of sensor S15 are formed. Tab 1004 can be wrapped around inside the glove (as indicated by the arrow) so that it coincides with the fingertip of the glove. Thus, any forces acting on the fingertip of the glove (e.g., by virtue of the fingertip coming into contact with a surface) will be detected by sensor S15. As will be appreciated, such sensors may be integrated with a sensor array for the back of the hand as shown in FIG. 10. Alternatively, such sensors may be implemented as separate array for the palm and fingertips.

Figure 11:
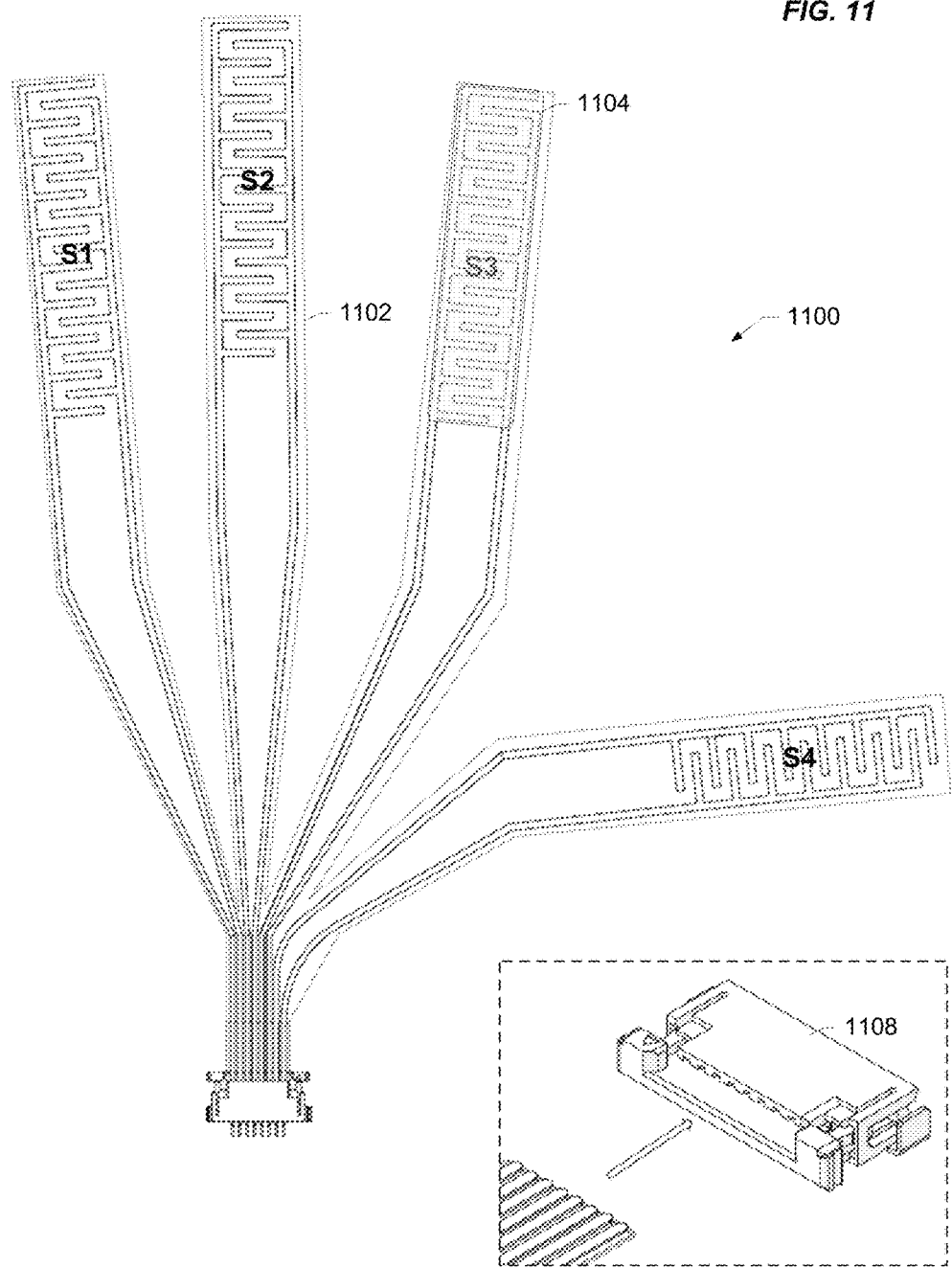
FIG. 11 shows another implementation of a sensor array.

FIG. 11 shows an alternative design for a sensor array 1100 for use in a sensor glove which includes only four elongated sensors; S1-S3 for the three middle fingers, and S4 for the thumb. As will be appreciated, this simpler design may be easier and/or cheaper to manufacture and may be sufficient or even more well-suited for some applications than the designs described above with reference to FIGS. 3 and 7. Nevertheless, sensor array 1100 operates similarly to the sensor arrays described and may be constructed using either approach. According to a particular implementation, substrate 1102 is constructed from a TPU material and the conductive traces are screen printed on substrate 1102 using a conductive flexible ink as described above with reference to FIGS. 7 and 8. Patches of a piezoresistive material (e.g., the Eeonyx fabric discussed above) are placed in contact with the conductive traces at the locations of sensors S1-S4. See for example, piezoresistive patch 1104 at sensor S3. A second substrate of the TPU material (not shown) is placed over array 1100, and the assembly is heated to thermally bond the components together, fixing the piezoresistive patches in contact with their respective sensor traces.

As with sensor array 700, a stiffener (not shown) may be adhered to substrate 1102 near the terminations of the conductive traces to allow for the insertion of the assembly into a connector 1108. As discussed above, use of the stiffener allows for connection of sensor array 1100 to any of a wide variety of industry standard connectors including, for example, the Molex connector 0522710869. Also as discussed above with reference to sensor array 700, stiffeners (not shown) may be placed in alignment with at least some of the piezoresistive patches and the corresponding trace patterns of sensor array 1100 for the purpose of amplifying the signals generated by the corresponding sensors.

FIGS. 12-14C illustrate another class of implementations for use in a sensor glove. Referring to the partially exploded view of FIG. 12, sensor system 1200 includes five digit assemblies 1202 (one for each finger or digit of the hand) and four abductor assemblies 1204 (one for each space between each pair of adjacent digits). These assemblies are connected to a circuit board 1206 on which is implemented the circuitry (not shown) for energizing and reading signals from the knuckle sensors and abductor sensors on each assembly. Digit assemblies 1202 are interconnected via substrate 1208 and abductor assemblies 1204 are interconnected via substrate 1210. Substrates 1208 and 1210 are secured to opposite sides of circuit board 1206 to form sensor system 1200. Conductors on substrates 1208 and 1210 provide connections between conductors on digit assemblies 1202 and abductor assemblies 1204 and corresponding conductors on circuit board 1206 (not shown). Sensor system 1200 is secured by top enclosure 1209 and ergonomic back plate 1211 and is aligned with the back of a hand inserted in a sensor glove 1300 as illustrated in FIG. 13.

Each digit assembly 1202 includes two knuckle sensors, each knuckle sensor being formed using a strip of piezoresistive material 1212 (e.g., a fabric) in contact with a group of sensor traces (obscured by material 1212 in FIG. 12) on the surface of a flexible dielectric substrate 1214. Routing traces 1216 by which signals are transmitted to and received from the individual sensors are adjacent the opposite surface of substrate 1214 from the sensor trace groups (i.e., the underside of substrate 1214 in the figure). Routing traces 1216 are connected to the sensor traces through substrate 1214, e.g., using vias. Substrate 1214 is depicted as being transparent so that routing traces 1216 on its underside are at least partially visible. Each knuckle sensor generates a sensor signal that represents the degree of bend in the corresponding knuckle.

Figure 12:
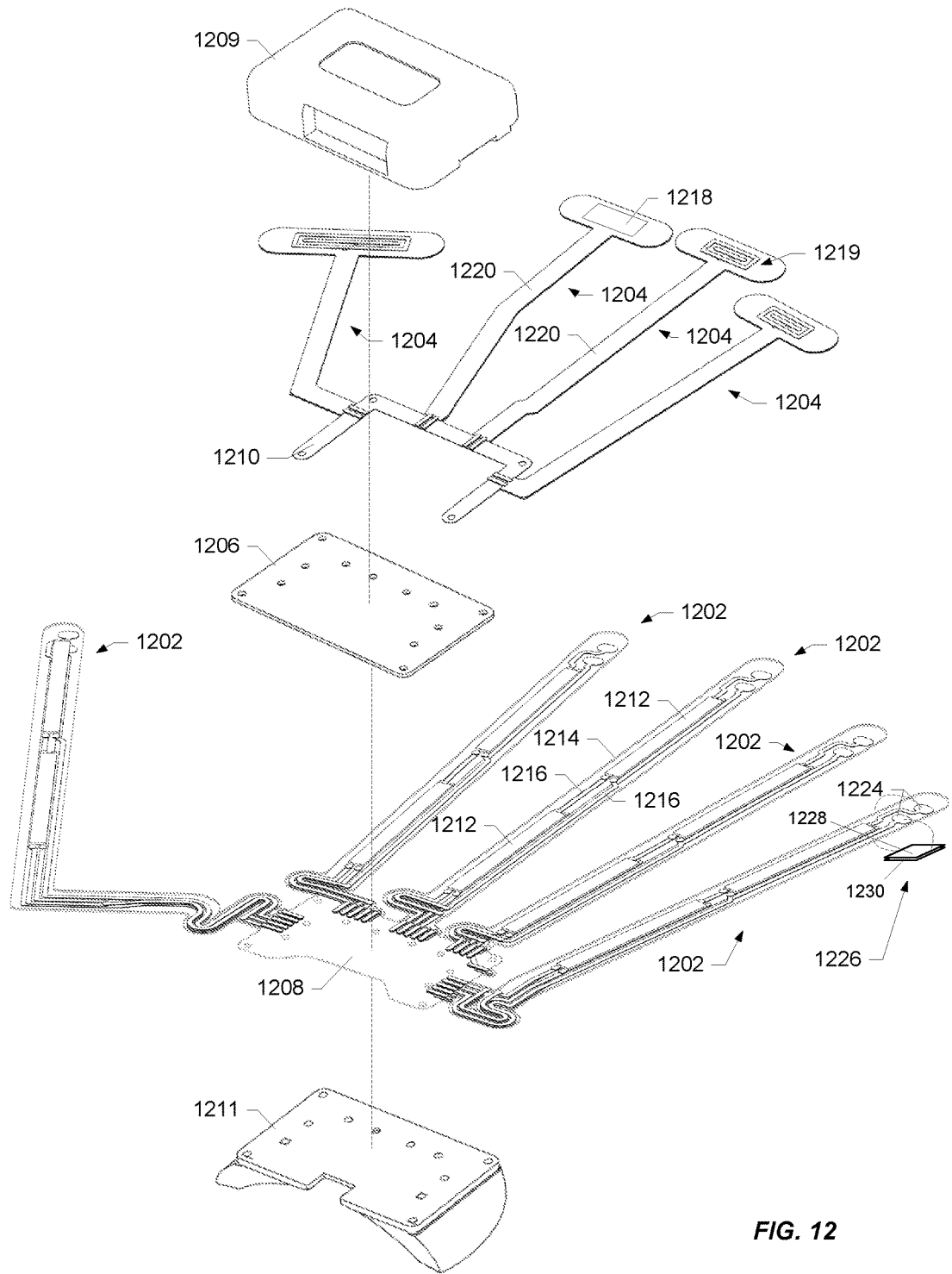

Each abductor assembly 1204 includes one abductor sensor formed using a strip of piezoresistive material 1218 (only one of which is shown in FIG. 12), e.g., a fabric, in contact with a group of sensor traces 1219 (one set of which is obscured by material 1218) on the surface of a flexible dielectric substrate 1220. Routing traces (not shown) by which signals are transmitted to and received from the abductor sensor are adjacent the opposite surface of substrate 1220 from the sensor trace group (i.e., the underside of substrate 1220 in the figure). The routing traces are connected to sensor traces 1219 through substrate 1220, e.g., using vias. Each abductor sensor generates a sensor signal that represents the spread angle between two adjacent digits. The orientation of sensor system 1200 within a glove may be understood with reference to FIG. 13.

As shown in FIG. 13, each digit assembly 1302 extends along the back of the glove and along one of the corresponding fingers (referring to the thumb as one of the fingers). As a particular finger bends, the degree of bend of its knuckles are represented by the sensor signals generated by the corresponding knuckle sensors. And as will be understood from the figure, when the fingers of the hand are together, the portion of each abductor assembly 1304 including the abductor sensor is bent back on itself almost 180 degrees (e.g., like a taco shell or a "v") with the center line of the bend being aligned with the crux of the two corresponding adjacent digits. The abductor sensor is considered to be "at rest" in this position. As the fingers are spread apart, the abductor sensor flattens out and stretches, generating a corresponding sensor signal representing the spread angle.

The individual sensors on the digit and abductor assemblies may be energized and interrogated as described above with reference to FIG. 3 using sensor circuitry such as that described with reference to FIG. 4. That is, each of the sensors includes two traces. One of the traces receives a drive signal, and the other transmits the sensor signal to the sensor circuitry. As discussed above, the sensor signal may be generated using a voltage divider in which one of the resistors of the divider includes the resistance between the two traces through the intervening piezoresistive material, and the other is included with the sensor circuitry. As the resistance of the piezoresistive material changes with applied force or pressure, the sensor signal also varies as a divided portion of the drive signal.

And as will be understood, the responses of the individual sensors in sensor systems enabled by the present disclosure may exhibit variation relative to each other as well as the corresponding sensors in similar systems. According to some implementations, calibrated sensor data are stored (e.g., in memory 407 of processor 406) that represent the response of each of the sensors. Such data ensure consistency and accuracy in the way the sensor outputs are processed and used to represent the motion and articulation of the parts of the hand. During calibration, the output of each sensor (e.g., as captured by ADC 404) is measured for a range of known input forces corresponding to specific positions of the hand. In this way, a set of data points for each sensor is captured (e.g., in a table in memory 407) associating ADC values with corresponding finger positions. The data set for each sensor may capture a value (or an offset value) for many (or even every) of the possible values of the ADC output. Alternatively, fewer data points may be captured and the sensor circuitry may use interpolation to derive force values for ADC outputs not represented in the data set.

The calibration data for each abductor sensor represent a range of the spread of the corresponding pair of fingers with a range of data values. The calibration data for each knuckle sensor represent a range of the bend of the corresponding knuckle with a range of data values. According to a particular implementation, calibration involves holding the hand in various positions and storing data values for those positions. For example, the user might be instructed (e.g., in a video or animation) to hold her hand out relaxed with the fingers together, make a fist, spread the fingers out, etc. Data values for each sensor may then be captured for each position.

According to a particular implementation, the calibration data capture two positions of the range for each sensor. These positions may be, for example, at the extreme ends of each range. For example, for an abductor sensor, the two positions might be (1) the pair of fingers together and (2) the pair of fingers spread apart as far as possible. Similarly, for a knuckle sensor, the two positions might be (1) the knuckle straight and (2) the knuckle bent as far as possible. Interpolation (e.g., linear interpolation) is then used at run time to determine positions in the range between the extremes for each knuckle and abductor sensor. These calibration data can be stored across sessions. And because such data can be user-specific, this might include the storing of multiple sets; one for each unique user. Alternatively, the calibration data can be regenerated for each session, e.g., by running the user through the various hand positions of the calibration routine.

According to some implementations, the sensor circuitry on circuit board 1206 includes an inertial measurement unit (IMU) (not shown) that includes a 3-axis accelerometer, a 3-axis gyroscope, and a 3-axis magnetometer. The information from these components is blended by the IMU to give the attitude of the hand, i.e., pitch, roll, and yaw. Translation, i.e., movement of the hand in x, y, and z, may be tracked using one or more cameras (e.g., gaming system cameras), one or more ultrasonic sensors, one or more electromagnetic sensors, etc., to determine the position of the glove in space. Thus, using the information generated by the sensor system, the IMU, and any translation sensing system, the position, attitude, and finger articulations of the user's hand can be captured. An example of an IMU that may be employed with various implementations is the BNO055 provided by Bosch Sensortec GmbH of Reutlingen/Kusterdingen, Germany. Other examples of suitable IMUs are provided by InvenSense, Inc. of San Jose, Calif., and ST Microelectronics of Geneva, Switzerland.

In the implementation depicted in FIG. 12, each digit assembly also includes a haptic actuator (not shown for clarity) which is connected to its own set of routing traces (partially visible) via pads 1224. The haptic actuators are aligned with each fingertip for the purpose of creating the sensation that the fingertip is in contact with an object or a surface (e.g., in a virtual space or at a remote location) thereby giving the user a sense of feel. Because sensor system 1200 is aligned with the back of the hand, the haptic actuators are connected to pads 1224 via conductors (not shown) that wrap around the finger.

According to a particular implementation, each actuator is a flexible metal membrane (e.g., a kapton-mylar film) stretched over a rigid substrate. The membrane shrinks or expands based on a voltage applied by the sensor circuitry via pads 1224. The haptic actuators can be thought of as tiny "speakers" that are driven with different waveforms to simulate different surfaces, signaling that the fingers have contacted something in the virtual world or at the remote location. The waveforms for these contact events depend on the nature of the surface being simulated, the number of fingertips contacting the surface, the rate of movement across the virtual surface, etc. In some cases, accompanying audio may be provided to enhance the perception of the contact. Examples of haptic actuators that may be used with various implementations include those provided by Novasentis Inc. of Berkeley, Calif.

Figure 14A:
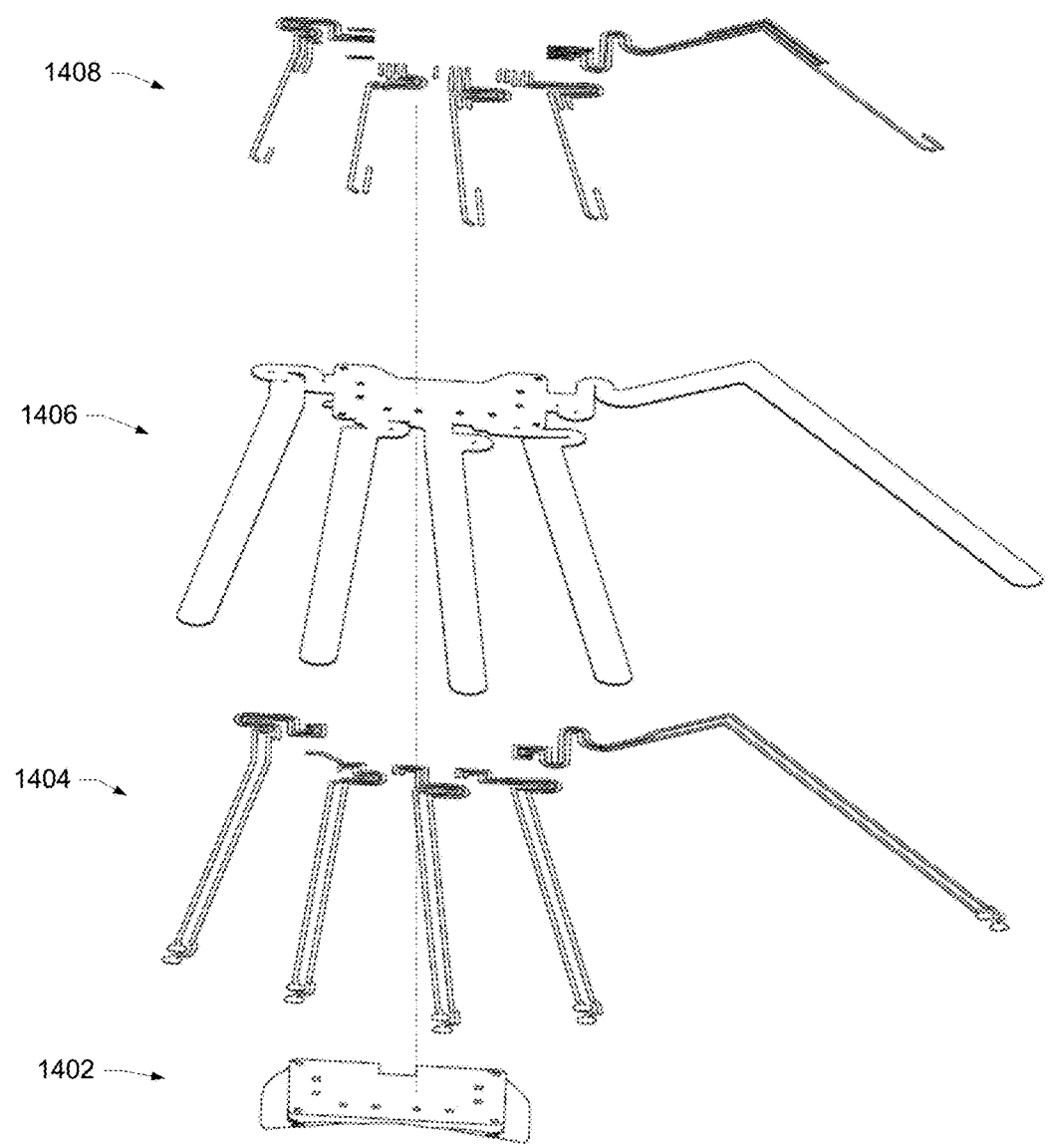
Figure 14B:
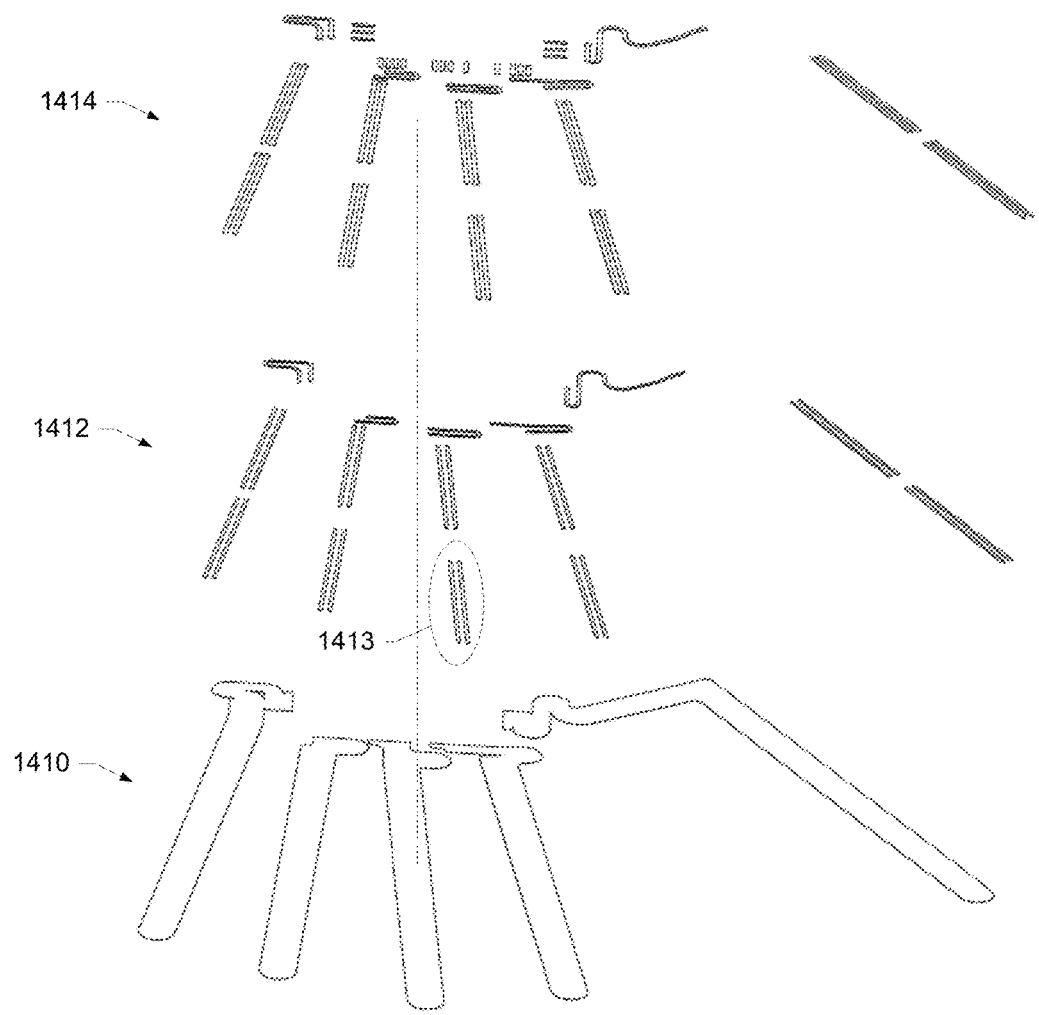
Figure 14C:
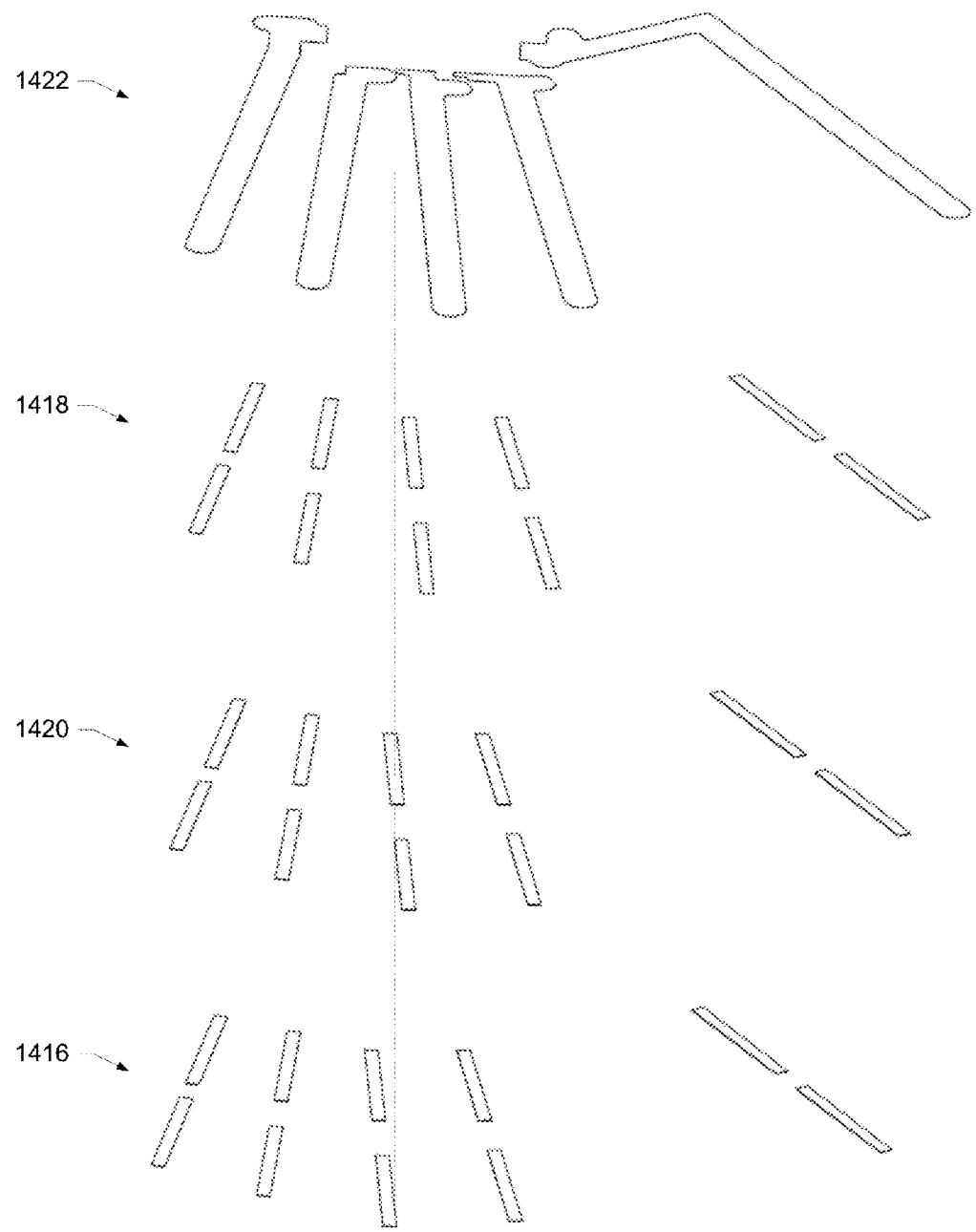

FIGS. 14A-14C show a stack of components of a sensor system that includes the knuckle sensors and haptic actuators. The components relating to the abductor sensors are not shown for clarity. However, it will be understood that the abductor assemblies may be formed similarly to the depicted digit assemblies in terms of the materials and the ordering of the components (without the components relating to the haptic actuators).

Referring to FIG. 14A, ergonomic back plate 1402 is shown at the bottom of the stack relative to the orientation of the figure. Back plate 1402 has a curved surface that conforms to the back of the user's hand. Haptic bus lines 1404 (for connection to the haptic actuators which are not shown) are printed with conductive ink on one side of PET substrate 1406. Sensor bus lines 1408 (including pads for connection to the sensor circuitry circuit board) that are used to energize and read signals from each of the knuckle sensors are printed with conductive ink on the other side of PET substrate 1406.

Referring to FIG. 14B, PET substrates 1410 are placed over sensor bus lines 1408 and PET substrate 1406. Sensor traces 1412 (including some traces to connect to the bus lines) are printed in conductive ink on PET substrates 1410 (and partially on PET substrate 1406 to connect with bus lines 1408). Each parallel pair of traces (e.g., 1413) on PET substrates 1410 corresponds to a knuckle sensor. A carbon passivation layer 1414 is printed over sensor traces 1412, and exposed portions of bus lines 1408 to protect the conductive traces from tarnishing and creeping. Dielectric strips may be placed over portions of the bus traces to insulate them from the sensor traces and the piezoresistive material.

Referring to FIG. 14C, piezoresistive fabric strips 1416 are placed in contact with each pair of sensor traces 1412 to form the knuckle sensors. Each fabric strip 1416 has a PET strip 1418 applied as a stiffener that is secured using pressure sensitive adhesive (PSA) 1420. PET 1418 makes fabric 1416 asymmetrically stiffer, resisting the bend of the fabric, causing it to distort, thereby enhancing the bend signal and helping to achieve the desired sensor response and dynamic range. As will be appreciated, a variety of materials of varying stiffness and/or thickness can be used as stiffeners depending on the desired response and dynamic range. TPU strips 1422 are placed over the knuckle sensors and heated to thermally bond the components together, fixing the piezoresistive strips in contact with their respective sensor traces.

As mentioned above, sensor traces 1412 are printed such that portions of the sensor traces are on PET substrates 1410 and other portions are contacting and connecting with bus lines 1408 on the underlying PET substrate 1406. Connections between sensor traces 1412 and bus lines 1408 may also be made through PET substrate 1406, e.g., using vias. And although the knuckle sensors are depicted as using two parallel traces other trace group configurations are contemplated. For example, sensor traces having interdigitated extensions are employed with some implementations as discussed above. Another example of such an implementation is shown in FIGS. 15 and 16.

Figure 15:
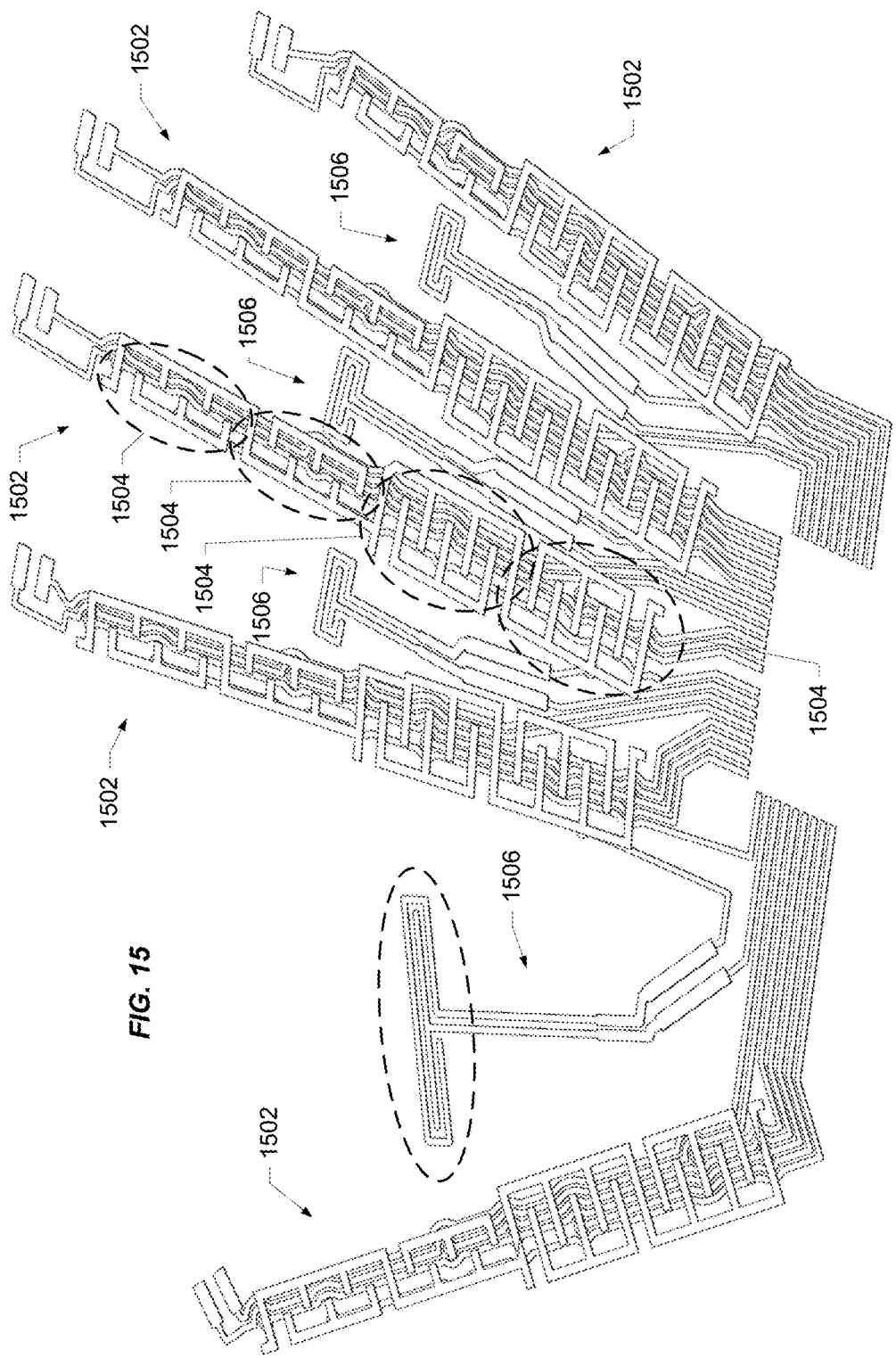

FIG. 15 shows the sensor traces and bus lines of a sensor system 1500 without other layers and components so as not to obscure details of these structures. Each of the five digit assemblies 1502 includes four knuckle sensors 1504 as indicated on the digit assembly corresponding to the middle finger. Having two sensors per knuckle may allow for finer detection and/or representation of motion. Four abductor assemblies 1506 are also shown.

According to this class of implementations and as depicted in FIG. 16, bus lines 1602 (which include both sensor and haptic bus lines) are printed in conductive ink on one side of a TPU substrate 1604. Sensor traces 1606 are printed in conductive ink on the other side of TPU substrate 1604 and connected to the corresponding bus lines through TPU substrate 1604, e.g., using vias. This assembly is then placed in contact with piezoresistive fabric, e.g., in the shape of a glove blank (not shown). These components are then heated, securing the sensor traces 1606 to the piezoresistive fabric from which a sensor glove is then made. Abductor assemblies 1608 (of which only the traces are shown) may be similarly constructed. Alternatively, because of their relatively simple structures, abductor assemblies 1608 may be formed on the piezoresistive fabric, e.g., printed using conductive ink and insulators (for the bus lines extending to and from the abductor sensors).

As should be appreciated with reference to the foregoing description, the applications for sensor gloves enabled by the present disclosure are numerous and diverse. As mentioned above, the action of a human hand in such a sensor glove may be translated to control systems, devices, and processes in both the real and virtual worlds. Using a sensor glove, a human can interact with objects in a virtual space, having utility in video and online gaming, as well as educational and artistic applications. For example, a sensor glove may be used to simulate a surgical procedure, playing of a virtual musical instrument, conducting of a virtual orchestra, painting of a virtual work of art, etc. Translation of the movements of a human hand into the virtual world could support more realistic computer aided animation. Industrial applications might include remote control of manufacturing apparatus or robotics handling hazardous materials. As will be appreciated from the diversity of these examples, the range of applications is virtually limitless. The scope of this disclosure should therefore not be limited by reference to specific applications.

It will be understood by those skilled in the art that changes in the form and details of the implementations described herein may be made without departing from the scope of this disclosure. In addition, although various advantages and aspects may have been described with reference to particular implementations, the scope of this disclosure should not be limited by reference to such advantages and aspects.

What is claimed is:

1. A sensor system for integration with a glove, comprising:
    a plurality of digit assemblies, each digit assembly being configured for alignment with a corresponding finger of the glove, each digit assembly including a flexible dielectric substrate, a plurality of sensor trace groups on a first surface of the flexible dielectric substrate, routing traces connected to each sensor trace group, the routing traces being adjacent a second surface of the flexible dielectric substrate opposite the first surface, and a plurality of patches of piezoresistive fabric, each patch being in direct contact with and forming a knuckle sensor with a corresponding one of the sensor trace groups; and circuitry configured to activate and receive a knuckle signal from each knuckle sensor on each digit assembly using the corresponding routing traces, each knuckle signal representing lateral stretching of the corresponding patch of piezoresistive fabric caused by bending of a knuckle in the corresponding finger of the glove, the circuitry also being configured to generate digital information using the knuckle signals, the digital information representing movement of a hand in the glove.

2. The sensor system of claim 1, wherein each digit assembly includes a thermoplastic material by which the corresponding patches of piezoresistive fabric are thermally bonded to the corresponding sensor trace groups.

3. The sensor system of claim 1, wherein the sensor trace groups of each digit assembly and the routing traces of each digit assembly comprise flexible conductive ink.

4. The sensor system of claim 1, wherein each sensor trace group of each digit assembly includes two substantially parallel sensor traces aligned with a longitudinal axis of the corresponding digit assembly.

5. The sensor system of claim 1, wherein each sensor trace group of each digit assembly includes two sensor traces having interdigitated extensions.

6. The sensor system of claim 1, further comprising a plurality of stiffeners, each stiffener being associated with a corresponding one of the knuckle sensors, each stiffener being applied to the corresponding patch of piezoresistive fabric.

7. The sensor system of claim 1, wherein each digit assembly further includes a haptic actuator connected to a fingertip-end of the digit assembly and configured to provide tactile stimulation to a fingertip in the glove.

8. The sensor system of claim 7, wherein the tactile stimulation provided by each haptic actuator represents contact between the corresponding fingertip and an object or surface in a virtual environment or at a location remote from the sensor system.

9. The sensor system of claim 7, wherein each haptic actuator includes a flexible metal membrane stretched over a rigid substrate, and wherein the flexible metal membrane shrinks or expands in response to activation by the circuitry.

10. The sensor system of claim 7, wherein the circuitry is configured to activate each haptic actuator with each of a plurality of waveforms, each waveform representing one or both of a nature of a surface being simulated, or a rate of movement across the surface.

11. The sensor system of claim 1, wherein the circuitry is further configured to generate the digital information using calibration data that represent a range of motion for each knuckle sensor.

12. The sensor system of claim 11, wherein the circuitry is configured generate the digital information using the calibration data by interpolating between data values of the calibration data to generate position data for positions within the range of motion for each knuckle sensor.

13. The sensor system of claim 11, wherein the circuitry is configured to generate the calibration data for each user session, or wherein the circuitry is configured to save the calibration data for subsequent user sessions.

14. The sensor system of claim 1, wherein the digital information is configured for use by a computing device to control a virtual hand in a virtual environment, or wherein the digital information is configured for use by an electronic system to control a robotic device.

15. The sensor system of claim 1, further comprising a wireless transceiver configured to facilitate communication between the circuitry and a computing device.

16. The sensor system of claim 1, further comprising a plurality of abductor assemblies, each abductor assembly being configured for alignment with a corresponding pair of the fingers of the glove, each abductor assembly including a flexible dielectric substrate, a sensor trace group on the flexible dielectric substrate, routing traces connected to the sensor trace group, and a patch of piezoresistive fabric, the patch forming an abductor sensor with the corresponding sensor trace group, wherein the circuitry is further configured to activate and receive an abductor signal from each abductor sensor on each abductor assembly using the corresponding routing traces, each abductor signal representing spreading of digits in the corresponding pair of the fingers of the glove, and wherein the circuitry is configured to generate the digital information using the abductor signals.

17. The sensor system of claim 1, further comprising an inertial measurement unit configured to generate inertial data representing an attitude of the hand in the glove.

18. The sensor system of claim 17, wherein the inertial measurement unit includes an accelerometer, a gyroscope, and a magnetometer, and wherein the inertial data represents pitch, roll, and yaw of the hand in the glove.

19. A sensor system for integration with a glove, comprising:
 a plurality of digit assemblies, each digit assembly being configured for alignment with a corresponding finger of the glove, each digit assembly including a flexible dielectric substrate, a plurality of sensor trace groups on a first surface of the flexible dielectric substrate, routing traces connected to each sensor trace group, the routing traces being adjacent a second surface of the flexible dielectric substrate opposite the first surface, and piezoresistive fabric, the flexible dielectric substrate of each digit assembly being a thermoplastic material by which the piezoresistive fabric is thermally bonded to and in direct contact with the corresponding sensor trace groups thereby forming a plurality of knuckle sensors;
 a plurality of haptic actuators, each haptic actuator being disposed near a fingertip-end of a corresponding one of the digit assemblies and configured to provide tactile stimulation to a fingertip in the glove; and
 a circuit board to which the digit assemblies are connected, the circuit board including circuitry configured to activate and receive a knuckle signal from each knuckle sensor on each digit assembly using the corresponding routing traces, each knuckle signal representing lateral stretching of the corresponding piezoresistive fabric caused by bending of a knuckle in the corresponding finger of the glove, the circuitry also being configured to generate digital information using the knuckle signals, the digital information representing movement of a hand in the glove, the circuitry also being configured to activate each of the haptic actuators.

20. The sensor system of claim 19, wherein the sensor trace groups of each digit assembly and the routing traces of each digit assembly comprise flexible conductive ink.

21. The sensor system of claim 19, wherein each sensor trace group of each digit assembly includes two substantially parallel sensor traces aligned with a longitudinal axis of the corresponding digit assembly.

22. The sensor system of claim 19, wherein each sensor trace group of each digit assembly includes two sensor traces having interdigitated extensions.

23. The sensor system of claim 19, further comprising a plurality of stiffeners, each stiffener being associated with a corresponding one of the knuckle sensors, each stiffener being applied to the corresponding piezoresistive fabric.

24. The sensor system of claim 19, wherein the circuitry is further configured to generate the digital information using calibration data that represent a range of motion for each knuckle sensor.

25. The sensor system of claim 24, wherein the circuitry is configured generate the digital information using the calibration data by interpolating between data values of the calibration data to generate position data for positions within the range of motion for each knuckle sensor.

26. The sensor system of claim 24, wherein the circuitry is configured to generate the calibration data for each user session, or wherein the circuitry is configured to save the calibration data for subsequent user sessions.

27. The sensor system of claim 19, wherein the digital information is configured for use by a computing device to control a virtual hand in a virtual environment, or wherein the digital information is configured for use by an electronic system to control a robotic device.

28. The sensor system of claim 19, further comprising a wireless transceiver configured to facilitate communication between the circuitry and a computing device.

29. The sensor system of claim 19, further comprising a plurality of abductor assemblies connected to the circuit board, each abductor assembly being configured for alignment with a corresponding pair of the fingers of the glove, each abductor assembly including a flexible dielectric substrate, a sensor trace group on the flexible dielectric substrate, routing traces connected to the sensor trace group, and piezoresistive fabric, the flexible dielectric substrate of each abductor assembly being thermoplastic material by which the piezoresistive fabric is thermally bonded to the corresponding sensor trace group thereby forming an abductor sensor, wherein the circuitry is further configured to activate and receive an abductor signal from each abductor sensor on each abductor assembly using the corresponding routing traces, each abductor signal representing spreading of digits in the corresponding pair of the fingers of the glove, and wherein the circuitry is configured to generate the digital information using the abductor signals.

30. The sensor system of claim 19, wherein the tactile stimulation provided by each haptic actuator represents contact between the corresponding fingertip and an object or surface in a virtual environment or at a location remote from the sensor system.

31. The sensor system of claim 19, wherein each haptic actuator includes a flexible metal membrane stretched over a rigid substrate, and wherein the flexible metal membrane shrinks or expands in response to activation by the circuitry.

32. The sensor system of claim 19, wherein the circuitry is configured to activate each haptic actuator with each of a plurality of waveforms, each waveform representing one or both of a nature of a surface being simulated, or a rate of movement across the surface.

33. The sensor system of claim 19, further comprising an inertial measurement unit configured to generate inertial data representing an attitude of the hand in the glove.

34. The sensor system of claim 33, wherein the inertial measurement unit includes an accelerometer, a gyroscope, and a magnetometer, and wherein the inertial data represents pitch, roll, and yaw of the hand in the glove.

* * * * *